United States Patent [19]

Nakatani et al.

[11] Patent Number: 4,599,362

[45] Date of Patent: * Jul. 8, 1986

[54] 2-ARYL-ETHYL ETHER DERIVATIVES AND INSECTICIDAL AND ACARICIDAL AGENTS CONTAINING SAID DERIVATIVES

[75] Inventors: Kiyoshi Nakatani, Tokyo; Satoshi Numata, Kanagawa; Tsuneo Inoue, Kanagawa; Akira Hosono, Kanagawa; Kengo Oda, Kanagawa; Yutaka Kubota, Kanagawa; Hajime Tachibana, Kanagawa; Takatoshi Udagawa, Kanagawa; Masatoshi Gohbara, Kanagawa, all of Japan

[73] Assignee: Mitsuitoatsu Chemicals, Inc., Chiyoda, Japan

[*] Notice: The portion of the term of this patent subsequent to Aug. 9, 2000 has been disclaimed.

[21] Appl. No.: 552,871

[22] Filed: Nov. 18, 1983

Related U.S. Application Data

[63] Continuation of Ser. No. 304,964, Sep. 23, 1981, abandoned.

[30] Foreign Application Priority Data

Oct. 9, 1980 [JP] Japan ................. 55-140600

[51] Int. Cl.$^4$ ............... A01N 43/30; A01N 31/14; C07C 43/267
[52] U.S. Cl. .................... 514/721; 568/637; 568/633; 568/49; 568/609; 568/328; 568/334; 568/586; 560/56; 560/65; 549/445; 549/362; 514/452; 514/464; 514/520; 514/532; 514/679; 514/682; 514/712; 558/424
[58] Field of Search .......... 568/636, 637, 633, 49, 568/609, 328, 334, 586; 424/341; 514/452, 464, 520, 532, 679, 682, 712, 721; 560/56, 65; 260/465 F; 549/445, 362

[56] References Cited

U.S. PATENT DOCUMENTS 4,073,812 2/1978 Bull et al. ................. 568/637
4,153,731 5/1979 Karrer ..................... 568/636
4,397,864 8/1983 Nakatani et al. ........... 568/636 X

OTHER PUBLICATIONS

Gysin, Chimia, vol. 8 (1954) 205–220.
Metcalf et al., Agricultural & Food Chemistry vol. 12 (1964) 231–236.
Yamamoto et al., Pesticide Design (1979) 79.
Ikeuchi et al., Advances in Pesticide Science Part 3 (1978) 470–474.
Elliott, M. et al., "Synthetic Pyrethroids-A New Class of Insecticide", Chem. Soc. Reviews, vol. 7, #4, pp. 473–505 (1978).

Primary Examiner—Bernard Helfin
Attorney, Agent, or Firm—Browdy and Neimark

[57] ABSTRACT

The present invention relates to 2-arylethyl ether or thioether derivatives represented by the following general formula [I]:

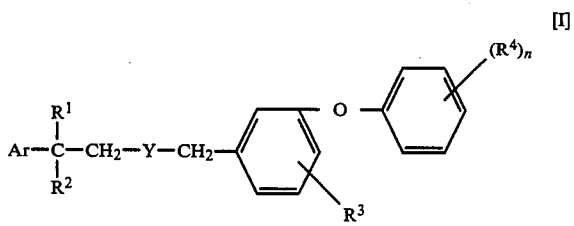

wherein Ar stands for an aryl group, $R^1$ stands for straight or branched chain alkyl group of 1 to 6 carbons, $R^2$ stands for a hydrogen atom, or a methyl or ethyl group, $R^3$ stands for a halogen atom, or a methyl or methoxyl group, $R^4$ stands for a hydrogen or halogen atom, or a lower alkyl or lower alkoxy group, and n is an integer of 1 or 2 with the proviso that when n is 2, the groups $R^4$ may be the same or different, and Y stands for an oxygen or sulfur atom, and also to processes for the preparation of these ethers or thioethers and a use of these ethers or thioethers.

These compounds of the present invention have excellent insecticidal and acaricidal activities while the toxicity of these compounds are very low.

25 Claims, No Drawings

2-ARYL-ETHYL ETHER DERIVATIVES AND INSECTICIDAL AND ACARICIDAL AGENTS CONTAINING SAID DERIVATIVES

This application is a continuation of application Ser. No. 304,964 filed Sept. 23, 1981 and now abandoned.

DETAILED DESCRIPTION OF THE INVENTION

The present invention relates to novel 2-arylethyl ether or thioether derivatives, processes for the preparation thereof, and insecticidal and acaricidal agents containing these novel compounds.

More specifically, in accordance with one aspect of the present invention, there are provided 2-arylethyl ether or thioether derivatives represented by the following general formula [I]:

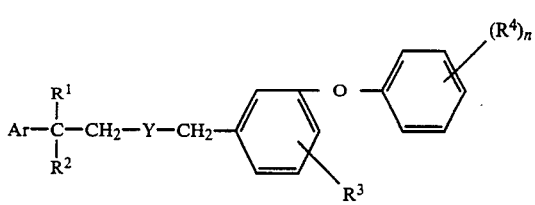

wherein Ar stands for an aryl group, $R^1$ stands for a straight or branched chain alkyl group of 1 to 6 carbons, $R^2$ stands for a hydrogen atom, or a methyl or ethyl group, $R^3$ stands for a halogen atom, or a methyl or methoxyl group, $R^4$ stands for a hydrogen or halogen atom, or a lower alkyl group or a lower alkoxy group, and n is an integer of 1 or 2 with the proviso that when n is 2, the groups $R^4$ may be the same or different, and Y stands for an oxygen or sulfur atom.

In accordance with another aspect of the present invention, there are provided processes for the preparation of 2-arylethyl ether or thioether derivatives represented by the above general formula [I], which comprises reacting a compound represented by the following general formula [III]:

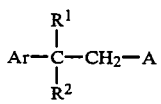

with a compound represented by the following general formula [IV]:

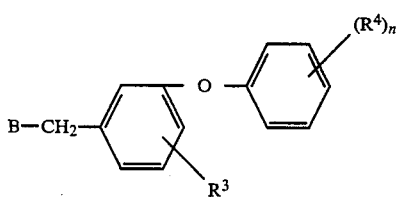

wherein Ar, $R^1$, $R^2$, $R^3$, $R^4$ and n are as defined above, and one of the groups A and B stands for a halogen atom and the other group is a group Y-M in which Y is as defined above and M stands for a hydrogen atom or an alkali metal or alkaline earth metal atom, or both A and B stand for a hydroxyl group.

In accordance with still another aspect of the present invention, there are provided insecticidal and acaricidal agents with low toxicity comprising 2-arylethyl ethers represented by the above general formula [I] and/or 2-arylethyl thioethers represented by the above general formula [I].

Insecticides have taken very important roles in improving productivities in various fields of agriculture. Development of organic synthetic agricultural chemicals changed completely the food situation for man, and agricultural chemicals have made great contributions to prevention of infectious diseases through the medium of insect pests.

However, uses of organochlorine insecticides represented by DDT and BHC are now limited because they are left in applied environments for a long time after application. Organophosphorous insecticides and carbamate insecticides developed as substitutes for these organochlorine insecticides are now used widely in various fields, but a variety of insect pests having acquired resistances to these chemicals have already appeared and insect pests which can hardly be controlled grow in certain territories. The problem of control of chemical-resistant insect pests will expand and become serious.

For the purpose of maintaining and developing civilization of the mankind established up to the present, it is important to continuously supply foods sufficiently and stably, and in order to attain this object, it is eagerly desired to develop chemicals having an excellent insecticidal activity.

Under such background, synthetic pyrethroid insecticides have attracted attention, because they have an excellent insecticidal activity and are very effective for controlling insect pests having acquired resistances to organophosphorous insecticides or carbamate insecticides while they have low toxicity to men and animals. However, these synthetic pyrethroid insecticides have a fatal defect in that the fish toxicity is very high, and the application ranges of these chemicals are strictly limited because of this fatal defect. Moreover, these synthetic pyrethroid insecticides are much more expensive than other synthetic insecticides heretofore developed.

These defects should be eliminated in agricultural chemicals which will be developed for the future. More specifically, it is desired to develop insecticides which have a high safety, are readily decomposed without being left in applied environments, hence do not cause any environmental pollution, have a high activity of controlling insect pests having acquired a resistance to insecticides and are manufactured at a low cost.

Research has been made with a view to developing insecticidal and acaricidal agents satisfying the foregoing requirements, and it has been found that specific 2-phenylpropyl ether or thioether derivatives have high insecticidal and acaricidal activities, are excellent in their fast-acting property and residual activity, are low toxicity to not only men and animals but also fishes and can be supplied at a relatively low cost.

The present research was continued for obtaining active compounds and also for confirming insecticidal and acaricidal characteristics of these compounds, and it was found that according to an appropriate combination of two alcohol residues in the abovementioned ether or thioether derivatives, these compounds can posses selective and non-selective activities to insect pests belonging to orders of Coleoptera, Lepidoptera, Orthoptera, Hemiptera, Isoptera, Diptera and Acarine and these compounds have a broad insecticidal spectrum and that very excellent insecticidal compositions having a very low toxicity to men and animals can be prepared from these compounds. It also was found that certain of these compounds are relatively low in their toxicity to fish.

The present invention has now been completed based on these findings.

The compounds of the present invention have an active structure quite different from those of the conventional agricultural chemicals. They have an excellent insecticidal activity to sanitary insect pests such as fly, mosquito and cockroach and agricultural insect pests such as planthoppers, leafhoppers, worms, moths, leaf holders, aphids, borers and mites, especially green rice leafhopper, and furthermore, they are effective for controlling stored grain insect pests such as grain mite, Indian meal moth and rice weevil, animal-parasitic mites and lice, and other insect pests. Furthermore, the compounds of the present invention are excellent in their fast-acting property and residual activity and have a flushing effect. Moreover, the compounds of the present invention have not only a knock-down effect to kill insect pests but also a repellent action of insect pests from hosts. Still further, the compounds of the present invention are advantageous in that the phytotoxicity to plants of Solanacede, which is observed in Fenvalerate, one of the typical instances of synthetic pyrethroids, is not observed at all. In addition, the compounds of their present invention are very low in the toxicity to mammals. And moreover, many of the compounds of the present invention have a substantially high safety to fish and they are suitably applied for controlling insect pests in paddy fields and aquatic insect pests such as larvae of mosquitoes and gnats and also are used for aerial application over broad districts including lakes, marshes, ponds and rivers without a fear of extermination of fish.

Accordingly, insecticidal and acaricidal compositions comprising the compounds of the present invention can be applied very widely in various fields and have a very high controlling effect to agricultural and horticultural insect pests, stored grain insects, sanitary insect pests, household insect pests, forest insect pests and aquatic insect pests. Moreover, they are very safe and can be supplied at low costs in the form of various formulations.

The 2-arylethyl ether and thioether derivatives represented by the general formula [I] according to the present invention are novel compounds, and among them there are 2-aryl-2-alkylethyl ether and thioether derivatives wherein one straight or branched chain alkyl group of 1 to 6 carbons is substituted at 2-position carbon of the ethyl group, and there are 2-aryl-2,2-dialkylethyl ether and thioether derivatives wherein a methyl or ethyl group and a straight or branched chain alkyl group of 1 to 6 carbons are disubstituted at 2-position carbon of the ethyl group. More specifically, the preferable compounds are 2-ethyl derivatives, 2-methyl-2-ethyl derivatives and 2,2-dimethyl derivatives.

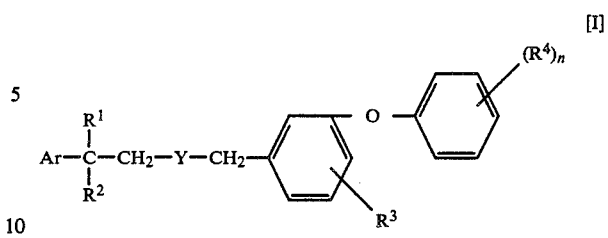

wherein Ar, $R^1$, $R^2$, Y, $R^3$, $R^4$ and n are as defined above.

In the general formula above, the aryl group Ar includes aromatic hydrocarbon groups such as phenyl, naphthyl, anthryl and phenanthryl groups, which may be unsubstituted or substituted with the same or different substituents selected from the substituents described hereinafter. As the substituent, there can be mentioned, for example, a halogen atom, a nitro group, a cyano group, a formyl group, or a substituted or unsubstituted lower alkyl, alkenyl, alkynyl, aryl, lower alkoxy, cycloalkyloxy, alkenyloxy, alkynyloxy, aryloxy, lower alkylthio, alkenylthio, alkynylthio, lower acyl, alkoxycarbonyl, alkenyloxycarbonyl, alkynyloxycarbonyl, alkylsulfinyl, methylenedioxy, ethylenedioxy group or a polymethylene group having 3 to 5 carbon atoms, and the aryl group may be mono-substituted or poly-substituted with the same or different substituents. From the industrial viewpoint, unsubstituted phenyl groups, or mono- to tri-substituted phenyl groups having the same or different substituents selected from a halogen atom, a nitro group, a cyano group, a lower alkyl group, a lower haloalkyl group, a lower alkoxy group, a lower haloalkoxy group, a methylenedioxy group and a lower alkylthio group are preferred.

Specific examples of the aryl group are mentioned below though aryl groups that can be used in the present invention are not limited to those exemplified below.

As specific examples of the aryl group, there can be mentioned a phenyl group, a 4-methylphenyl group, a 3,4-dimethylphenyl group, a 4-trifluoromethylphenyl group, a 3-methylphenyl group, a 3-trifluoromethylphenyl group, a 4-chlorphenyl group, a 3,4-dichlorophenyl group, a 4-nitrophenyl group, a 4-methylthiophenyl group, a 4-methoxyphenyl group, a 3,4-dimethoxyphenyl group, a 4-trifluoromethylthiophenyl group, a 3,4-methylenedioxyphenyl group, a 3,4-(difluoromethylenedioxy)-phenyl group, a 4-cyanophenyl group, a 4-fluorophenyl group, a 4-bromophenyl group, a 3,4-difluorophenyl group, a 3,4-dibromophenyl group, a 4-chloro-3-fluorophenyl group, a 3-chloro-4-fluorophenyl group, a 3-chloro-4-methylphenyl group, a 3-bromo-4-chlorophenyl group, a 4-difluoromethoxyphenyl group, a 3,4-bis(difluoromethoxy)phenyl group, a 4-trifluoromethoxyphenyl group, a 3,4-bis(trifluoromethoxy)phenyl group, a 4-methoxy-3,5-dimethylphenyl group, a 3,4-trifluoroethylenedioxyphenyl group, a 4-tert-butylphenyl group, a 4-ethylphenyl group, a 4-isopropylphenyl group, a 3,4-difluoroethylenedioxyphenyl group, a 4-isopropenylphenyl group, a 4-vinylphenyl group, a 4-(2,2-dichlorovinyl)phenyl group, a 4-chloro-3-methylphenyl group, a 3-bromo-4-fluorophenyl group, 2-naphthyl group, a 3-fluoro-4-bromophenyl group, a 4-fluoro-3-methylphenyl group, a 3-fluoro-4-methylphenyl group, a 3-bromo-4-methylphenyl group, a 3,4-diethylphenyl group, a 3,4-diisopropylphenyl group, a 3-ethyl-4-methylphenyl group, a 4-isopropyl-3-methylphenyl group, a 4-methoxymethoxyphenyl group, a 4-allylphenyl group, a 4-acetylphenyl group, a 4-ethoxycarbonylphenyl group, a 4-ethoxyphenyl group, a 1,2,3,4-tetrahydronaphthalen-7-yl group, a 3,5-dichloro-4-methylphenyl group, an indan-5-yl group, a 4-propargylphenyl group, a 3-methoxy-4-methylphenyl group, a 4-methoxymethylphenyl group, a 4-(1-chloroethenyl)phenyl group, a 4-(2-chloroallyl)phenyl group, a 4-isobutyrylphenyl group, a 4-methoxycarbonylphenyl group, a 3-nitro-4,5-dimethylphenyl group, a 3-ethoxy-4-bromophenyl group, a 3-chloro-4-methoxyphenyl group, a 4-bromo-3-chlorophenyl group, a 3,4-(di-tert-butyl)phenyl group, a 4-ethyl-3-methylphenyl group, a 4-tert-butyl-3-methylphenyl group, a 4-(1,1,2,2-tetrafluoroethoxy)phenyl group, a 4-(2,2-dichlorovinyloxy)phenyl group, a 4-(2,2,2-trifluoroethoxy)phenyl group, a 4-pentafluoroethoxyphenyl group, a 4-(chlorodifluoromethoxy)phenyl group, a 4-(chlorofluoromethoxy)-phenyl group, a 4-dichlorofluoromethoxy phenyl group, a 4-(1,1-difluoroethoxy)-phenyl group, a 4-(1,2,2-trichloro-1,2-difluoroethoxy)-phenyl group, a 4-(2-bromo-1,1,2,2-tetrafluoroethoxy)-phenyl group, a 4-(2-propynyloxy)phenyl group, a 4-(1-propynyloxy)phenyl group, a 4-allyloxyphenyl group, a 4-ethynyloxyphenyl group, a 4-(2-chloroethynyl)phenyl group, a 4-(n-propoxy)phenyl group, a 4-(isopropoxy)phenyl group, a 4-cyclopentyloxyphenyl group, a 4-(n-pentyloxy)phenyl group, a 4-isobutoxy phenyl group, a 4-iodophenyl group, a 4-vinyloxyphenyl group, a 4-biphenyl group, a 4-(n-butoxy)phenyl group, a 4-(sec-butoxy)phenyl group, a 6-methyl-2-naphthyl group, a 4-phenoxyphenyl group, a 4-(2-iodo-1,1-difluoroethoxy)-phenyl group, a 4-cyclohexyloxyphenyl group, a 3-chloro-4-ethoxyphenyl group, a 4-formylphenyl group, 4-ethoxymethylphenyl group, a 4-(1-ethoxyethyl)phenyl group, a 4-(1-methoxyethyl)-phenyl group, a 4-ethoxy-3-methylphenyl group, a 4-(2-methyl-1-propenyl)phenyl group, a 4-(1,2,2-trichlorovinyloxy)phenyl group, a 3,4-diethoxyphenyl group, a 4-ethynylphenyl group, a 4-ethoxy-3,5-dimethylphenyl group, a 4-ethoxy-3-methoxyphenyl group, a 4-ethylthiophenyl group, a 4-(2,2,2-trifluoroethoxycarbonyl)phenyl group, a 4-(2-chloroethoxy)-phenyl group, a 4-(1-butene-2-yl)phenyl group, a 4-(2-butene-2-yl)phenyl group, a 3,5-dichlorophenyl group, a 4-ethoxy-3-chlorophenyl group, a 3-ethoxyphenyl group, a 4-ethylthiophenyl group, a 4-isopropylthiophenyl group, and a 4-methoxymethylthiophenyl group.

As specific examples of the substituted phenoxybenzyl group, there can be mentioned a 3-phenoxy-4-fluorobenzyl group, a 3-phenoxy-4-chlorobenzyl group, a 3-phenoxy-4-bromobenzyl group, a 3-(4-fluorophenoxy)-4-fluorobenzyl group, a 3-(4-bromophenoxy)-4-fluorobenzyl group, a 3-(4-chlorophenoxy)-4-fluorobenzyl group, a 3-(3-bromophenoxy)-4-fluorobenzyl group, a 3-(3-chlorophenoxy)-4-fluorobenzyl group, a 3-(4-methylphenoxy)-4-fluorobenzyl group, a 3-(4-methoxyphenyl)-4-fluorobenzyl group, a 3-(2-fluorophenoxy)-4-fluorobenzyl group, a 3-phenoxy-5-methoxybenzyl group, a 3-(3-methoxyphenoxy)-4-fluorobenzyl group, a 3-phenoxy-2-fluorobenzyl group, a 3-(4-fluorophenoxy)-2-fluorobenzyl group, a 3-(3-fluorophenoxy)-2-fluorobenzyl group, a 3-(2-fluorophenoxy)-2-fluorobenzyl group, a 3-(4-fluorophenoxy)-5-fluorobenzyl group, a 3-(3-fluorophenoxy)-4-fluorobenzyl group, a 3-(3-fluorophenoxy)-5-fluorobenzyl group, a 3-(2-fluorophenoxy)-5-fluorobenzyl group, a 3-phenoxy-4-methylbenzyl group, a 3-(4-methylphenoxy)-5-fluorobenzyl group, a 3-(3-methoxyphenoxy)-5-fluorobenzyl group, a 3-(2-fluorophenxy)-6-fluorobenzyl group, a 3-(3-fluorophenoxy)-6-fluorobenzyl group, a 3-(4-fluorophenoxy)-6-fluorobenzyl group, a 3-phenoxy-2-fluorobenzyl group, a 3-phenoxy-5-fluorobenzyl group, a 3-phenoxy-6-fluorobenzyl group, a 3-phenoxy-6-chlorobenzyl group, a 3-phenoxy-5-fluorobenzyl group, a 3-phenoxy-2-chlorobenzyl group, a 3-(3-methylphenoxy)-4-chlorobenzyl group, a 3-(4-fluorophenoxy)-4-chlorobenzyl group, a 3-phenoxy-5-chlorobenzyl group, a 3-phenoxy-6-bromobenzyl group, a 3-phenoxy-4-bromobenzyl group, a 3-phenoxy-5-bromobenzyl group and a 3-(4-ethoxyphenoxy)-4-fluorobenzyl group.

Typical examples of the compounds according to the present invention will now be described. Of course, the compounds included in the scope of the present invention are not limited to those exemplified below.

Incidentally, in the case where the groups of $R^1$ and $R^2$ in the general formula [I] are different, the compounds contain an asymmetric carbon atom and there are present optical isomers. These optical isomers and mixtures thereof are included in the scope of the present invention.

Examples of the compounds included in the scope of the present invention are as follows.

3-(4-Fluorophenoxy)-4-fluorobenzyl 2-(4-chlorophenyl)-2-methylpropyl ether and thioether 3-Phenoxy-4-fluorobenzyl 2-phenyl-2-methylpropyl ether and thioether 3-Phenoxy-4-chlorobenzyl 2-(4-chlorophenyl)-2-methylpropyl ether and thioether 3-Phenoxy-4-fluorobenzyl 2-(4-methoxyphenyl)-2-methylpropyl ether and thioether 3-Phenoxy-4-fluorobenzyl 2-(3,4-dimethylphenyl)-2-methylpropyl ether and thioether 3-(4-Fluorophenoxy)-4-fluorobenzyl 2-(4-methoxyphenyl)-2-methylpropyl ether and thioether 3-Phenoxy-4-fluorobenzyl 2-(4-chlorophenyl)-2-ethylbutyl ether and thioether 3-Phenoxy-4-fluorobenzyl 2-(4-chlorophenyl)-butyl ether and thioether 3-Phenoxy-6-chlorobenzyl 2-(4-chlorophenyl)-2-methylpropyl ether and thioether 3-Phenoxy-4-fluorobenzyl 2-(4-chlorophenyl)-3-methylbutyl ether and thioether 3-(4-Fluorophenoxy)-4-fluorobenzyl 2-(3,4-dichlorophenyl)-2-methylbutyl ether and thioether 3-Phenoxy-5-methoxybenzyl 2-(4-chlorophenyl)-2-methylpropyl ether and thioether 3-(3-Chlorophenoxy)-4-fluorobenzyl 2-(4-chlorophenyl)-2-methylpropyl ether and thioether 3-(3-Chlorophenoxy)-4-florobenzyl 2-(3,4-dimethylphenyl)-2,3-dimethylbutyl ether and thioether 3-Phenoxy-4-fluorobenzyl 2-(4-chlorophenyl)-2-methylpropyl ether and thioether 3-(2-Fluorophenoxy)-4-fluorobenzyl 2-(3-chloro-4-fluorophenoxy)-2-methylpropyl ether and thioether 3-(2-Fluorophenoxy)-4-fluorobenzyl 2-(4-chlorophenyl)-2-methylpropyl ether and thioether 3-(4-Fluorophenoxy)-4-chlorobenzyl 2-(3,4-dimethoxyphenyl)-2-methylhexyl ether and thioether 3-Phenoxy-4-fluorobenzyl 2-(naphthalene-2-yl)-2-methylpropyl ether and thioether 3-Phenoxy-4-fluorobenzyl 2-(4-methoxy-3,5-dimethylphenyl) 2-methylpropyl ether and thioether 3-Phenoxy-4-fluorobenzyl 2-(4-tert-butylphenyl)-2-methylpropyl ether and thioether 3-(4-Methoxyphenoxy)-4-fluorobenzyl 2-(4-chlorophenyl)-2-methylpropyl ether and thioether 3-Phenoxy-4-fluorobenzyl 2-(3,4-dichlorophenyl)-2-methylpropyl ether and thioether 3-(4-Bromophenoxy)-4-fluorobenzyl 2-(4-chlorophenyl)-2-methylpropyl ether and thioether 3-Phenoxy-4-fluorobenzyl 2-(4-isopropenylphenyl)-butylether and thioether 3-Phenoxy-4-fluorobenzyl 2-(3-trifluoromethylphenyl)-2-methylpropyl ether and thioether 3-Phenoxy-4-fluorobenzyl 2-(4-bromophenyl)-2-methylpropyl ether and thioether 3-Phenoxy-4-methylbenzyl 2-(4-chlorophenyl)-2-methylpropyl ether and thioether 3-Phenoxy-4-fluorobenzyl 2-(3-methylphenyl)-2-methylpropyl ether and thioether 3-Phenoxy-5-fluorobenzyl 2-(3,4-diethylphenyl)-2-methylpropyl ether and thioether 3-Phenoxy-4-fluorobenzyl 2-[(1,2,3,4-tetrahydro) naphthalene-7-yl]-2-methylpropyl ether and thioether 3-Phenoxy-4-fluorobenzyl 2-(indane-5-yl)-2-methylpropyl ether and thioether 3-(3-Fluorophenoxy)-4-fluorobenzyl 2-(3-methoxy-4-methylphenyl)-2-methylpropyl ether and thioether 3-Phenoxy-4-fluorobenzyl 2-(3-ethoxy-4-bromophenyl)-2-methylpropyl ether and thioether 3-Phenoxy-4-fluorobenzyl 2-(4-chlorophenyl)-2-methylbutyl ether and thioether 3-Phenoxy-4-fluorobenzyl 2-[3,4-(difluoromethylenedioxy)-phenyl]-2-methylpropyl ether and thioether 3-Phenoxy-4-fluorobenzyl 2-(4-chlorophenyl)-2,3,3-trimethylbutyl ether and thioether 3-Phenoxy-4-fluorobenzyl 2-(4-difluoromethoxyphenyl)-2-methylpropyl ether and thioether 3-(3-Methylphenoxy)-4-fluorobenzyl 2-(4-chlorophenyl)-2-methylpropyl ether and thioether 3-(3-Chlorophenoxy)-5-fluorobenzyl 2-(3-nitro-4,5-dimethylphenyl)-2-methylpropyl ether and thioether 3-(2-Fluorophenoxy)-4-fluorobenzyl 2-(4-methylthiophenyl)-2-methylpropyl ether and thioether 3-(3-Fluorophenoxy)-5-fluorobenzyl 2-(3-chloro-4-methoxyphenyl)-2-methylpropyl ether and thioether 3-Phenoxy-6-bromobenzyl 2-(4-methylphenyl)-2-methylpropyl ether and thioether 3-(4-Fluorophenoxy)-4-fluorobenzyl 2-(3,4-dichlorophenyl)-2-methylpropyl ether and thioether 3-Phenoxy-2-fluorobenzyl 2-(4-chlorophenyl)-2,3-ether and thioether 3-Phenoxy-4-fluorobenzyl 2-(4-chlorophenyl)-2,3-dimethylbutyl ether and thioether 3-Phenoxy-6-bromobenzyl 2-(4-chlorophenyl)-2-methylpropyl ether and thioether 3-(4-Fluorophenoxy)-2-fluorobenzyl 2-phenyl-2-methylpropyl ether and thioether 3-Phenoxy-4-fluorobenzyl 2-(4-methylthiophenyl)-2-methylpropyl ether and thioether 3-Phenoxy-4-fluorobenzyl 2-(4-methylphenyl)-2-methylpropyl ether and thioether 3-(4-Fluorophenoxy)-5-fluorobenzyl 2-(4-chlorophenyl)-2-methylpropyl ether and thioether 3-Phenoxy-4-fluorobenzyl 2-(4-fluorophenyl)-2-methylpropyl ether and thioether 3-Phenoxy-5-fluorobenzyl 2-(4-chlorophenyl)-2-methylpropyl ether and thioether 3-Phenoxy-2-fluorobenzyl 2-(4-trifluoromethylphenyl)-2-methylpropyl ether and thioether 3-Phenoxy-4-fluorobenzyl 2-(4-nitrophenyl)-2-methylpropyl ether and thioether 3-Phenoxy-5-chlorobenzyl 2-(4-chlorophenyl)-2-methylpropyl ether and thioether 3-Phenoxy-6-chlorobenzyl 2-(4-methylphenyl)-2-methylpropyl ether and thioether 3-Phenoxy-6-fluorobenzyl 2-(4-methylphenyl)-2-methylpropyl ether and thioether 3-Phenoxy-4-fluorobenzyl 2-(3,4-methylenedioxyphenyl)-2-methylpropyl ether and thioether 3-(3-Chlorophenoxy)-4-fluorobenzyl 2-(4-chlorophenyl)-butyl ether and thioether 3-Phenoxy-6-fluorobenzyl 2-(4-chlorophenyl)-2-methylpropyl ether and thioether 3-Phenoxy-4-fluorobenzyl 2-(4-chloro-3-methylphenyl)-2-methylpropyl ether and thioether 3-Phenoxy-4-fluorobenzyl 2-(4-trifluoromethylthiophenyl)-2-methylpropyl ether and thioether 3-Phenoxy-4-fluorobenzyl 2-(4-difluoromethoxyphenyl)-butyl ether and thioether 3-Phenoxy-4-fluorobenzyl 2-(4-cyanophenyl)-2-methylpropyl ether and thioether 3-Phenoxy-4-fluorobenzyl 2-(3,4-difluorophenyl)-2-methylpropyl ether and thioether 3-Phenoxy-4-fluorobenzyl 2-(4-ethoxyphenyl)-2-methylpropyl ether and thioether 3-Phenoxy-4-fluorobenzyl 2-(3,4-dibromophenyl)-2-methylpropyl ether and thioether 3-Phenoxy-4-fluorobenzyl 2-(4-trifluoromethoxyphenyl)-2-methylpropyl ether and thioether 3-Phenoxy-4-fluorobenzyl 2-(4-ethylphenyl)-2-methylpropyl ether and thioether 3-Phenoxy-4-fluorobenzyl 2-(4-isopropylphenyl)-2-methylpropyl ether and thioether 3-Phenoxy-4-fluorobenzyl 2-(4-ethoxyphenyl)-butylether and thioether 3-Phenoxy-4-fluorobenzyl 2-(4-pentafluoroethoxyphenyl)-2-methylpropyl ether and thioether 3-Phenoxy-4-fluorobenzyl 2-(4-difluoromethoxyphenyl)-2,3-dimethylbutyl ether and thioether 3-Phenoxy-4-fluorobenzyl 2-(4-ethoxyphenyl)-2-methylbutyl ether and thioether 3-Phenoxy-4-fluorobenzyl 2-(4-allylphenyl)-2-methylpropyl ether and thioether 3-Phenoxy-4-fluorobenzyl 2-(4-methoxymethylphenyl)-2-methylpropyl ether and thioether 3-Phenoxy-5-chlorobenzyl 2-(4-methylphenyl)-2-methylpropyl ether and thioether 3-Phenoxy-4-fluorobenzyl 2-(4-isobutyrylphenyl)-2-methylpropyl ether and thioether 3-Phenoxy-4-fluorobenzyl 2-(3,5-dichlorophenyl)-2-methylpropyl ether and thioether 3-Phenoxy-4-fluorobenzyl 2-(3,4-di-tert-butylphenyl)-2-methylpropyl ether and thioether 3-Phenoxy-4-fluorobenzyl 2-(4-difluoromethoxyphenyl)-2-methylbutyl ether and thioether 3-Phenoxy-4-fluorobenzyl 2-(4-chloro-3-methylphenyl)-2-methylpropyl ether and thioether 3-Phenoxy-4-fluorobenzyl 2-[3,4-bis(trifluoromethoxy)phenyl]-2-methylpropyl ether and thioether 3-Phenoxy-4-fluorobenzyl 2-(4-methoxy-3,5-dimethylphenyl)-2-methylpropyl ether and thioether 3-Phenoxy-4-fluorobenzyl 2-[4-(2,2-dichlorovinyloxy)phenyl]-2-methylpropyl ether and thioether 3-Phenoxy-4-fluorobenzyl 2-(4-ethoxyphenyl)-2,3-dimethylbutyl ether and thioether 3-Phenoxy-4-fluorobenzyl 2-[4-(1,1,2,2-tetrafluoroethoxy)phenyl]-2-methylpropyl ether and thioether 3-Phenoxy-4-fluorobenzyl 2-(4-chloro-3-bromophenyl)-2-methylpropyl ether and thioether
3-Phenoxy-4-fluorobenzyl 2-[4-(2,2,2-trifluoroethoxy)phenyl]-2-methylpropyl ether and thioether
3-Phenoxy-4-fluorobenzyl 2-(6-methyl-2-naphthyl)-2-methylpropyl ether and thioether
3-Phenoxy-4-fluorobenzyl 2-[4-(2,2-dichlorovinyl)phenyl]-2-methylpropyl ether and thioether
3-Phenoxy-4-fluorobenzyl 2-(3-fluoro-4-methylphenyl)-2-methylpropyl ether and thioether
3-Phenoxy-4-fluorobenzyl 2-(4-dichlorofluoromethoxyphenyl)-2-methylpropyl ether and thioether
3-Phenoxy-4-fluorobenzyl 2-(4-difluoromethoxyphenyl)-3-methylbutyl ether and thioether
3-Phenoxy-4-fluorobenzyl 2-(3-chloro-4-methylphenyl)-2-methylpropyl ether and thioether
3-Phenoxy-4-fluorobenzyl 2-(3-bromo-4-fluorophenyl)-2-methylpropyl ether and thioether
3-Phenoxy-4-fluorobenzyl 2-(4-bromo-3-fluorophenyl)-2-methylpropyl ether and thioether
3-Phenoxy-4-fluorobenzyl 2-(3-chloro-4-bromophenyl)-2-methylpropyl ether and thioether
3-Phenoxy-4-fluorobenzyl 2-(4-fluoro-3-methylphenyl)-2-methylpropyl ether and thioether
3-Phenoxy-4-fluorobenzyl 2-(3-fluoro-4-methylphenyl)-2-methylpropyl ether and thioether
3-Phenoxy-4-fluorobenzyl 2-(4-ethoxyphenyl)-3-methylbutyl ether and thioether
3-Phenoxy-4-fluorobenzyl 2-(3-bromo-4-methylphenyl)-2-methylpropyl ether and thioether
3-Phenoxy-4-fluorobenzyl 2-(4-isopropylphenyl)-2-methylpropyl ether and thioether
3-Phenoxy-4-fluorobenzyl 2-(3,4-diisopropylphenyl)-2-methylpropyl ether and thioether
3-Phenoxy-4-fluorobenzyl 2-(3-ethyl-4-methylphenyl)-2-methylpropyl ether and thioether
3-Phenoxy-4-fluorobenzyl 2-(4-ethyl-3-methylphenyl)-2-methylpropyl ether and thioether
3-Phenoxy-4-fluorobenzyl 2-(3-methyl-4-tert-butylphenyl)-2-methylpropyl ether and thioether
3-Phenoxy-4-fluorobenzyl 2-(4-isopropyl-3-methylphenyl)-2-methylpropyl ether and thioether
3-Phenoxy-4-fluorobenzyl 2-(4-n-propoxyphenyl)-2-methylpropyl ether and thioether
3-Phenoxy-4-fluorobenzyl 2-(4-n-propoxyphenyl)-2-methylbutyl ether and thioether
3-Phenoxy-4-fluorobenzyl 2-(4-isopropoxyphenyl)-2-methylpropyl ether and thioether
3-Phenoxy-4-fluorobenzyl 2-(4-isopropoxyphenyl)-2-methylbutyl ether and thioether
3-(4-Fluorophenoxy)-4-fluorobenzyl 2-(4-ethoxyphenyl)-2-methylpropyl ether and thioether
3-Phenoxy-4-fluorobenzyl 2-(4-acetylphenyl)-2-methylpropyl ether and thioether
3-Phenoxy-4-fluorobenzyl 2-(4-cyclopentyloxyphenyl)-2-methylpropyl ether and thioether
3-Phenoxy-4-fluorobenzyl 2-(4-n-pentyloxyphenyl)-2-methylpropyl ether and thioether
3-Phenoxy-4-fluorobenzyl 2-(4-isobutyloxyphenyl)-2-methylpropyl ether and thioether
3-Phenoxy-4-fluorobenzyl 2-(4-iodophenyl)-2-methylpropyl ether and thioether
3-Phenoxy-4-fluorobenzyl 2-(4-iodophenyl)-2-methylbutyl ether and thioether
3-(4-Bromophenoxy)-4-fluorobenzyl 2-(4-ethoxyphenyl)-2-methylpropyl ether and thioether
3-Phenoxy-4-fluorobenzyl 2-(4-vinyloxyphenyl)-2-methylpropyl ether and thioether
3-Phenoxy-4-fluorobenzyl 2-(4-biphenyl)-2-methylpropyl ether and thioether
3-Phenoxy-4-fluorobenzyl 2-(4-n-butoxyphenyl)-2-methylpropyl ether and thioether
3-Phenoxy-4-fluorobenzyl 2-(4-sec-butoxyphenyl)-2-methylpropyl ether and thioether
3-Phenoxy-4-fluorobenzyl 2-(4-phenoxyphenyl)-2-methylpropyl ether and thioether
3-Phenoxy-4-fluorobenzyl 2-(3-chloro-4-fluorophenyl)-2-methylpropyl ether and thioether
3-Phenoxy-4-fluorobenzyl 2-(4-cyclohexyloxyphenyl)-2-methylpropyl ether and thioether
3-Phenoxy-4-fluorobenzyl 2-[4(1,1-difluoro-2-iodoethoxy)phenyl]-2-methylpropyl ether and thioether
3-(4-Chlorophenoxy)-4-fluorobenzyl 2-(4-ethoxyphenyl)-2-methylpropyl ether and thioether
3-Phenoxy-4-fluorobenzyl 2-(3-chloro-4-ethoxyphenyl)-2-methylpropyl ether and thioether
3-Phenoxy-4-fluorobenzyl 2-[4-(1,1-difluoroethoxy)phenyl]-2-methylpropyl ether and thioether
3-Phenoxy-4-fluorobenzyl 2-(4-methoxymethylphenyl)-2-methylpropyl ether and thioether
3-Phenoxy-4-fluorobenzyl 2-(4-ethoxymethoxyphenyl)-2-methylpropyl ether and thioether
3-Phenoxy-4-fluorobenzyl 2-(3,4-dimethoxyphenyl)-2-methylpropyl ether and thioether
3-Phenoxy-4-fluorobenzyl 2-(4-ethoxymethylphenyl)-2-methylpropyl ether and thioether
3-Phenoxy-4-fluorobenzyl 2-[(4-methoxymethoxy)phenyl]-2-methylpropyl ether and thioether
3-Phenoxy-4-fluorobenzyl 2-[4-(1-ethoxyethoxy)phenyl]-2-methylpropyl ether and thioether
3-Phenoxy-4-fluorobenzyl 2-(4-ethoxycarbonylphenyl)-2-methylpropyl ether and thioether
3-Phenoxy-4-fluorobenzyl 2-[4-(1-methoxyethyl)phenyl]-2-methylpropyl ether and thioether
3-Phenoxy-4-fluorobenzyl 2-[4-(2-ethoxyethoxy)phenyl]-2-methylpropyl ether and thioether
3-Phenoxy-4-fluorobenzyl 2-(4-ethoxy-3-methylphenyl)-2-methylpropyl ether and thioether
3-Phenoxy-4-fluorobenzyl 2-[4-(2-methyl-1-propenyl)phenyl]-2-methylpropyl ether and thioether
3-Phenoxy-4-fluorobenzyl 2-[4-(1,2,2-trichlorovinyloxy)phenyl]-2-methylpropyl ether and thioether
3-Phenoxy-4-fluorobenzyl 2-(3,4-diethoxyphenyl)-2-methylpropyl ether and thioether
3-Phenoxy-4-fluorobenzyl 2-(4-ethynylphenyl)-2-methylpropyl ether and thioether
3-Phenoxy-4-fluorobenzyl 2-(4-ethoxy-3,4-dimethylphenyl)-2-methylpropyl ether and thioether
3-Phenoxy-4-fluorobenzyl 2-(4-propargyloxyphenyl)-2-methylpropyl ether and thioether
3-Phenoxy-4-fluorobenzyl 2-(4-ethoxy-3-methoxyphenyl)-2-methylpropyl ether and thioether
3-Phenoxy-4-fluorobenzyl 2-(3-ethoxyphenyl)-2-methylpropyl ether and thioether
3-Phenoxy-4-fluorobenzyl 2-(4-ethylthiophenyl)-2-methylpropyl ether and thioether
3-(4-Ethoxyphenoxy)-4-fluorobenzyl 2-(4-ethoxyphenyl)-2-methylpropyl ether and thioether
3-Phenoxy-4-fluorobenzyl 2-[4-(1-chlorovinyl)-phenyl]-2-methylpropyl ether and thioether
3-Phenoxy-4-fluorobenzyl 2-(4-vinylphenyl)-2-methylpropyl ether and thioether
3-Phenoxy-4-fluorobenzyl 2-[4-(2,2,2-trifluoroethoxycarbonyl)phenyl]-2-methylpropyl ether and thioether 3-Phenoxy-4-fluorobenzyl 2-[4-(2-chloroethoxy)-phenyl]-2-methylpropyl ether and thioether 3-Phenoxy-4-fluorobenzyl 2-[4-(1-methyl-1-propenyl)-phenyl]-2-methylpropyl ether and thioether 3-Phenoxy-4-fluorobenzyl 2-[4-(1-butene-2-yl)-phenyl]-2-methylpropyl ether and thioether 3-Phenoxy-4-fluorobenzyl 2-(4-isopropylthiophenyl)-2-methylpropyl ether and thioether 3-Phenoxy-4-fluorobenzyl 2-(4-methoxymethylthio-phenyl)-2-methylpropyl ether and thioether 3-Phenoxy-4-fluorobenzyl 2-[4-(2-fluoroethoxy)-phenyl]-2-methylpropyl ether and thioether and 3-Phenoxy-4-fluorobenzyl 2-[4-(3-iodopropargyloxy)-phenyl]-2-methylpropyl ether and thioether The preparation processes of the present invention will now be described in detail.

In the case where an alcohol or thiol of the general formula [III] in which A stands for Y-M (in which Y is as defined above and M stands for a hydrogen atom) is reacted with a halide of the general formula [IV] in which B stands for a halogen atom, the reaction is carried out in the presence of a base as an acid acceptor in an appropriate solvent at room temperature or under heating to give a desired 2-arylethyl ether or thioether derivative. As the base, there can be mentioned an alkali metal hydroxide, an alkaline earth metal hydroxide, an alkali metal hydride, an alkali metal alcoholate, an alkali metal oxide, an alkali metal carbonate, sodium amide and triethylamine. Furthermore, silver oxide may be used as the acid acceptor. As the solvent, there can be used, for example, water, aromatic hydrocarbons such as benzene, toluene and xylene, aliphatic hydrocarbons such as hexane, heptane and petroleum benzin, halogenated hydrocarbons such as chloroform and dichloromethane, aprotic polar solvents such as dimethylformamide and dimethylsulfoxide, ethers such as diisopropyl ether, diethyl ether, 1,2-dimethoxyethane, tetrahydrofuran and dioxane, nitriles such as acetonitrile and propionitrile, and ketones such as acetone and diisopropyl ketone. If a phase transfer catalyst represented by tetra-n-butyl ammonium bromide or triethylbenzyl ammonium chloride is used as the catalyst, the intended 2-arylethyl ether or thioether derivative can be obtained in a high yield.

In the case where an alcoholate or thioalcoholate of the general formula [III] in which A stands for a group Y-M (in which Y is as defined above and M is the metal atom defined above) is reacted with a halide of the general formula ]IV] in which B stands for a halogen atom, the reaction is carried out in a solvent as mentioned above at room temperature or under heating to give a desired 2-arylethyl ether or thioether derivative. When the reactivity is low, a catalytic amount of potassium iodide or copper iodide is preferably added.

In the case where an alcohol of the general formula [III] in which A stands for a hydroxyl group is reacted with an alcohol of the general formula [IV] in which B stands for a hydroxyl group, dehydration reaction is carried out in the presence of a catalyst to give a 2-arylethyl ether derivative. As the catalyst, there may be employed an acid catalyst such as sulfuric acid, hydrochloric acid, an aromatic sulfonic acid, sulfonyl chloride, boron trifluoride or aluminum chloride. Furthermore, there may be used iodine, a solid acid catalyst (aluminatitanium oxide or the like), dimethylsulfoxide, alumina, a sulfide or an ion exchange resin as the dehydrating catalyst. The reaction is preferably carried out under reflux in an inert solvent azeotropic with water, such as benzene or toluene, according to need.

Furthermore, a 2-arylethyl ether derivative can be obtained by reacting an alcohol of the general formula [III] in which A stands for a hydroxyl group with an alcohol of the general formula [IV] in which B stands for a hydroxyl group in the presence of a dehydrating agent, if necessary in the presence of a catalyst. As the dehydrating agent, there is preferably used an N,N-substituted carbodiimide, especially N,N-dicyclohexylcarbodiimide. For example, cuprous chloride is preferably used as the catalyst. The reaction is carried out in an appropriate inert solvent or diluent at room temperature or under heating. As the solvent or diluent, there may preferably be used ethers such as 1,2-diethoxyethane, dioxane and tetrahydrofuran, aprotic polar solvents such as dimethylformamide, hexamethylphosphoric triamide and dimethylsulfoxide, and ketones such as acetone, methylethyl ketone and cyclohexanone.

In the case where a halide of the general formula [III] in which A stands for a halogen atom is reacted with an alcohol or thiol or alcoholate or thioalcoholate of the general formula [IV] in which B stands for a group Y-M (in which Y and M are as defined above), the reaction can be carried out according to the same procedures as described above. Especially when a halide of the general formula [III] in which A stands for a halogen atom is reacted with an alcohol or thiol of the general formula [IV] in which B stands for Y-H (in which Y is as defined above), the reaction is carried out in the presence of a base as an acid acceptor in an aprotic polar solvent, preferably dimethylsulfoxide or sulfolane, under heating, whereby a desired 2-arylethyl ether or thioether derivative can be obtained in a high yield.

As another process for the preparation of 2-arylethyl ether derivatives, there can be mentioned a process in which a metal alcoholate or sulfonic acid ester of an alcohol of the general formula [III] in which A stands for a hydroxyl group is reacted with an alcohol of the general formula [IV] in which B stands for a hydroxyl group, and a process in which an alcohol of the general formula [III] in which A stands for a hydroxyl group is reacted with a metal alcoholate or sulfonic acid ester of an alcohol of the general formula [IV] in which B stands for a hydroxyl group. However, these processes are disadvantageous from the viewpoint of the yield of the desired product compound.

The starting substance represented by the general formula [III], in which A stands for Y-M (in which Y and M are as defined above) or a halogen atom, can be prepared according to a known process or a process similar to a known process disclosed in a reference. For example, an alcohol represented by the general formula [III] in which A stands for a hydroxyl group can be obtained by alkylating a corresponding arylacetonitrile of the formula Ar.CH$_2$.CN, in which Ar is as defined above, with a halogenated alkyl compound, hydrolyzing the obtained nitrile to a corresponding carboxylic acid and reducing the carboxylic acid. Furthermore, a halogenated compound of the general formula [III] in which A stands for a halogen atom and R$^1$ stands for a methyl group, obtained by adding a 2-alkylallyl halide to a substituted or unsubstituted aryl compound, can be converted to an alcohol as mentioned above. An alcohol can be converted to a thiol.

The preparation routes are diagrammatically shown below.

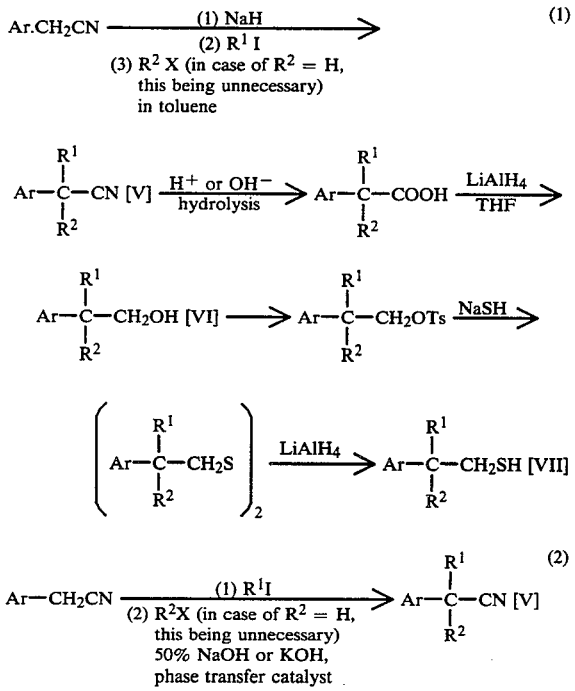

Reference: Roczniki Chem., 39 (9), 1223 (1965) (Pol)
[Chemical Abstract 64, 12595h (1966)]

Then, the preparation route (1) is adopted.

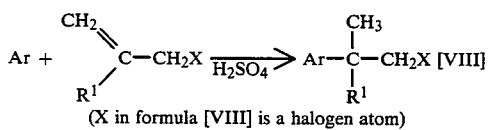

(X in formula [VIII] is a halogen atom)
Reference: Chem. Ber., 94, 2609 (1961)

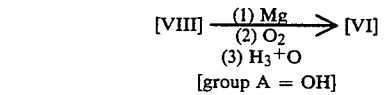

[group A = OH]
Reference: J. Am. Chem. Soc., 65, 1469 (1943)

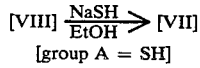

[group A = SH]

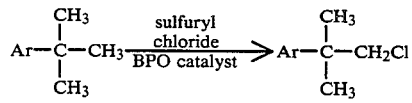

Reference: Chem. Ber., 94, 2609 (1961)

A compound of [VI] is synthesized according to route (3).

Furthermore, an alcohol of the general formula [III] in which A stands for a hydroxyl group may be prepared according to the process disclosed in Helvetica Chimica Acta, 54, 868 (1971).

A metal alcoholate or metal thioalcoholate of the general formula [III] in which A stands for a group Y-M in which Y and M are as defined above can easily be prepared according to a conventional method, for example, a process comprising reacting an alcohol or thiol of the general formula [III] in which A stands for a group Y-H in which Y is as defined above with a metal hydride such as sodium hydride.

A halide of the general formula [IV] in which B stands for a halogen atom or an alcohol of the general formula [IV] in which B stands for a hydroxyl group is known as an alcohol component of a synthetic pyrethroid or it may be prepared according to a known process disclosed in a reference. A thiol of the general formula [IV] in which B stands for —SH is prepared from an alcohol of the general formula [IV] in which B stands for a hydroxyl group according to a conventional method.

The process for the preparation of 2-arylethyl ether and thioether derivatives of the present invention will now be described in detail with reference to the following Synthesis Examples.

SYNTHESIS EXAMPLE 1

(Etherification Process A)

Preparation of 3-(4-bromophenoxy)-4-fluorobenzyl 2-(4-chlorophenyl)-2-methylpropyl ether is described.

To 20 ml of dry acetonitrile was added 0.90 g of sodium hydride (60% in oil), and a solution of 2.8 g of 2-(4-chlorophenyl)-2-methylpropyl alcohol in 10 ml of acetonitrile was added dropwise to the mixture at 50° C.

The mixture was refluxed for 30 minutes, and a solution of 6.6 g of 3-(4-bromophenoxy)-4-fluorobenzyl bromide in 10 ml of acetonitrile was added dropwise to the reaction mixture over a period of 10 minutes. The mixture was further refluxed for 1 hour, and the mixture was cooled to room temperature, poured into water and was extracted with toluene. The toluene extract was washed with a saturated aqueous solution of sodium chloride and dried over $Na_2SO_4$, and evaported under reduced pressure, and the obtained crude ether was purified by column chromatography on 150 g of silica gel (1:1 mixed solvent of toluene and n-hexane was used as eluent) to give 4.6 g of the desired ether (the yield was 65% of the theoretical yield).

$n_D^{20}$ 1.5806.

$\gamma_{max}^{film}$ (cm$^{-1}$) 1590, 1490, 1435, 1295, 1225, 1105, 1020, 830.

$\delta CCl_4$ (ppm): 1.29 (s, 6H), 3.32 (s, 2H), 4.32 (s, 2H), 6.7–7.5 (m, 11H).

Elementary Analysis Values as $C_{23}H_{21}BrClFO_2$: Calculated: C=59.56%, H=4.5%, Br=17.23%, Cl=7.65%, F=4.10% Found: C=59.85%, H=4.64%, Br=17.01%, Cl=7.77%, F=4.00%

SYNTHESIS EXAMPLE 2

(Etherification Process B)

Preparation of 3-phenoxy-4-fluorobenzyl 2-(4-methylphenyl)-2-methylpropyl ether is described.

To 20 ml of toluene was added 0.63 g of sodium hydride (60% in oil) and the mixture was refluxed, and a solution of 1.7 g of 2-(4-methylphenyl)-2-methylpropyl alcohol in 10 ml of 25% DMF/toluene was added dropwise to the mixture over a period of 15 minutes. The mixture was stirred for 10 minutes, and a solution of 3.0 g of 3-phenoxy-4-fluorobenzyl chloride in 10 ml of toluene was added dropwise to the mixture over a period of 20 minutes.

Then, the mixture was refluxed for 1.5 hours and cooled to room temperature, and poured into water.

The organic layer was separated, washed with water and dried over $Na_2SO_4$, and evaporated under reduced pressure, and the obtained crude ether was purified by column chromatography on 100 g of silica gel (1:1 mixed solvent of toluene and n-hexane was used as eluent) to give 2.7 g of the desired ether (the yield was 71% of the theoretical yield).

$n_D^{20}$ 1.5611.

$\gamma_{max}^{film}$ (cm$^{-1}$): 1600, 1500, 1435, 1290, 1225, 1105, 825, 695.

$\delta CCl_4$ (ppm): 1.30 (s, 6H), 2.27 (s, 3H), 3.34 (s, 2H), 4.34 (s, 2H), 6.8–7.4 (m, 12H).

Elementary Analysis Values as $C_{24}H_{25}FO_2$: Calculated: C=79.09%, H=6.91%, F=5.21% Found: C=79.23%, H=7.01%, F 5.42%

SYNTHESIS EXAMPLE 3

(Etherification Process C)

Preparation of 3-phenoxy-4-fluorobenzyl 2-(4-chlorophenyl)-2-methylpropyl ether is described.

To 20 g of a 50% aqueous solution of NaOH were added 6.0 g of 2-(4-chlorophenyl)-2-methylpropyl alcohol, 8.6 g of 3-phenoxy-4-fluorobenzyl bromide and 1.1 g of tetrabutyl ammonium bromide, and the mixture was stirred at 80° C. for 1 hour. The mixture was cooled to room temperature and poured into water, and the mixture was extracted with toluene and the toluene extract was washed with water and dried over $Na_2SO_4$, and evaporated under reduced pressure, and the obtained crude ether was purified by column chromatography on 250 g of silica gel (1:1 mixed solvent of toluene and n-hexane was used as eluent) to give 10.0 g of the desired ether (the yield was 80% of the theoretical yield).

$n_D^{20}$ 1.5710.

$\gamma_{max}^{film}$ (cm$^{-1}$): 1585, 1490, 1425, 1280, 1210, 1095, 1100, 820, 685.

$\delta CCl_4$ (ppm): 1.26 (s, 6H), 3.30 (s, 2H), 4.32 (s, 2H), 6.8–7.4 (m, 12H).

Elementary Analysis Values as $C_{23}H_{22}ClFO_2$: Calculated: C=71.77%, H=5.76%, Cl=9.21%, F=4.94% Found: C=71.95%, H=5.55%, Cl=9.31%, F=5.02%

SYNTHESIS EXAMPLE 4

(Etherification Process D)

Preparation of 3-phenoxy-4-fluorobenzyl 2-(3-methylphenyl)-2-methylpropylether is described.

To 20 ml of toluene were added 2 ml of concentrated sulfuric acid, 2.7 g of 3-phenoxy-4-fluorobenzyl alcohol and 2.1 g of 2-(3-methylphenyl)-2-methylpropylalcohol, and the mixture was refluxed for 6 hours (water formed by reaction was removed). The mixture was cooled to room temperature, and poured into water and the toluene layer was separated, washed with water, dried, and evaporated under reduced pressure, and the obtained crude ether was purified by column chromatography on 100 g of silica gel (1:1 mixed solvent of toluene and n-hexane was used as eluent) to give 1.9 g of the desired ether (the yield was 42% of the theoretical yield).

$n_D^{20}$ 1.5582. $\gamma_{max}^{film}$ (cm$^{-1}$): 1600, 1505, 1435, 1290, 1225, 1130, 710. $\delta CCl_4$ (ppm): 1.30 (s, 6H), 2.29 (s, 3H), 3.34 (s, 2H), 4.33 (s, 2H), 6.8–7.4 (m, 12H).

Elementary Analysis Values as $C_{24}H_{25}FO_2$: Calculated: C=79.09%, H=6.91%, F=5.21% Found: C=79.31%, H=7.02%, F=5.01%

SYNTHESIS EXAMPLE 5

(Etherification Process E)

Preparation of 3-phenoxy-4-fluorobenzyl 2-(4-chlorophenyl)-2-methylpropyl ether is described.

A mixture of 8.53 of 4-chloroneophyl chloride, 8.72 g of 3-phenoxy-4-fluorobenzyl alcohol, 3.9 g of 45% NaOH and 48 g of dimethyl sulfoxide was heated and stirred at 140° C. for 3 hours, and 1.8 g of 45% NaOH was further added, kept at the same temperature for 4 hours, poured into 500 ml of water and was extracted with benzene. The benzene extract was washed with water, dried over $Na_2SO_4$, and evaporated under reduced pressure and the obtained crude ether was purified by column chromatography on 250 g of silica gel (1:1 mixed solvent of toluene and n-hexane was used as eluent) to give 7.27 g of the desired ether (the yield was 77% of the theoretical yield based on consumed 4-chloroneophyl chloride).

$n_D^{20}$ 1.5710.

Infrared spectrum and NMR spectrum of this ether were identical with those of Synthesis Example 3.

SYNTHESIS EXAMPLE 6

(Etherification Process F)

Preparation of 3-phenoxy-6-chlorobenzyl 2-(4-chlorophenyl)-2-methylpropyl ether is described.

2.0 g of 2-(4-chlorophenyl)-2-methyl propyl alcohol, 3.5 g of 3-phenoxy-6-chlorobenzyl bromide, 20 g of 50% NaOH and 0.4 g of triethylbenzyl ammonium bromide were charged into 50 ml-separable flask and the mixture was stirred at 50° C. for 2 hours. The reaction mixture was cooled to room temperature, then water and benzene were added thereto and stirred with cooling by ice water. The benzene layer was separated, washed with water and dried over $Na_2SO_4$, and evaporated under reduced pressure, and the obtained crude ether was purified by column chromatography on 150 g of silica gel (1:1 mixed solvent of toluene and hexane was used as eluent to give 3.8 g of the desired ether (the yield was 87% of the theoretical yield).

$n_D^{19.5}$ 1.5854.

$\gamma_{max}^{film}$ (cm$^{-1}$): 1500, 1480, 1275, 1260, 1215, 1110, 1020, 830.

$\delta CCl_4$ (ppm): 1.29 (s, 6H), 3.44 (s, 2H), 4.49 (s, 2H), 6.7–7.5 (m, 12H).

SYNTHESIS EXAMPLE 7

(Etherification Process G)

Preparation of 3-phenoxy-4-fluorobenzyl 2-(4-chlorophenyl)-2,3-dimethylbutyl ether is described.

To 20 ml of toluene was added 0.60 g of sodium hydride (60% in oil) and the mixture was heated and refluxed, and a solution of 2.0 g of 2-(4-chlorophenyl)-2,3-dimethylbutyl alcohol in 10 ml of 40% DMF/toluene was added dropwise to the mixture over a period of 20 minutes. The mixture was stirred for 10 minutes and a solution of 3.5 g of 3-phenoxy-4-fluoro benzyl bromide in 10 ml of toluene was added dropwise to the mixture over a period of 10 minutes. The mixture was further heated and refluxed for 1 hour and cooled to room temperature, and poured into water. The toluene layer was separated, washed with water, dried over $Na_2SO_4$, and evaporated under reduced pressure and the obtained crude ether was purified by column chromatography on 120 g of silica gel (1:1 mixed solvent of toluene and hexane was used as eluent) to give 2.8 g of the desired ether (the yield was 72% of the theoretical yield).

$n_D^{19.9}$ 1.5656.

$\nu_{max}^{film}$ (cm$^{-1}$): 1610, 1530, 1510, 1450, 1300, 1230, 1140, 1120, 1030.

$\delta CCl_4$ (ppm): 0.62 (d, 3H, J=6.8 Hz), 0.85 (d, 3H, J=6.8 Hz), 1.19 (s, 3H), 1.9–2.3 (m, 1H), 3.34 (d, 1H, $J_{AB}$ = 8.8Hz)  ⎫
3.53 (d, 1H, $J_{AB}$ = 8.8Hz)  ⎬ AB type 4.30 (s, 2H), 6.7–7.4 (m, 12H).

SYNTHESIS EXAMPLE 8

3-Phenoxy-4-fluorobenzyl 2-(4-difluoromethoxyphenyl)-2-methylpropyl ether was synthesized according to the procedures described in Synthesis Example 3. $n_D^{20}$ 1.5405.

$\nu_{max}^{film}$ (cm$^{-1}$): 1590, 1490, 1280, 1210, 1130, 1045, 815, 685 $\delta$CCl$_4$ (ppm): 1.31 (s, 6H), 3.34 (s, 2H), 4.36(s, 2H), 6.40 (t, J=75 Hz, 1H), 6.8–7.4 (m, 12H)

Elementary Analysis Values as $C_{24}H_{23}F_3O_3$: Calculated: C=69.22%, H=5.57%, F=13.69% Found: C=69.52%, H=5.29% F=13.58%.

SYNTHESIS EXAMPLE 9

3-Phenoxy-4-fluorobenzyl 2-(4-chlorophenyl)-2-methylpropyl thioether was synthesized according to the procedures described in Synthesis Example 2. $n_D^{20.2}$ 1.5802.

$\nu_{max}^{film}$ (cm$^{-1}$): 1595, 1515, 1495, 1430, 1285, 1220, 1170, 1110, 1015, 970, 825, 755, 690.

$\delta$CCl$_4$ (ppm): 1.33 (s, 6H), 2.54 (s, 2H), 3.27 (s, 2H), 6.80–7.29 (m, 12H)

Typical instances of the compounds included in the scope of the present invention are shown in Table 1. Etherification was carried out according to the etherification process of from A to G described in Synthesis Examples.

TABLE 1

| Compound No. | Ar | R¹ | R² | Y | R³ | R⁴ | Etherification Process | Yield (%) | Physical Property Values |
|---|---|---|---|---|---|---|---|---|---|
| 1 | Cl–⟨phenyl⟩– | CH₃– | CH₃– | –O– | 4-F | 4'-F | C | 78 | $n_D^{20}$ 1.5600<br>$C_{23}H_{21}ClF_2O_2$<br>Calculated (%) / Found (%)<br>C: 68.57 / 68.36<br>H: 5.25 / 5.21<br>Cl: 8.80 / 8.89<br>F: 9.43 / 9.48 |
| 2 | ⟨phenyl⟩– | CH₃– | CH₃– | –O– | 4-F | H | F | 85 | $n_D^{20}$ 1.5654<br>$C_{23}H_{23}FO_2$<br>Calculated (%) / Found (%)<br>C: 79.51 / 78.99<br>H: 6.68 / 6.62<br>F: 5.47 / 5.52 |
| 3 | Cl–⟨phenyl⟩– | CH₃– | CH₃– | –O– | 4-Cl | H | C | 76 | $n_D^{20}$ 1.5850<br>$C_{23}H_{22}Cl_2O_2$<br>Calculated (%) / Found (%)<br>C: 68.83 / 68.90<br>H: 5.53 / 5.47<br>Cl: 17.67 / 17.73 |
| 4 | Cl–⟨phenyl⟩– | CH₃– | CH₃– | –S– | 4-F | H | B | 68 | $n_D^{20.2}$ 1.5802<br>$C_{23}H_{22}ClFOS$<br>Calculated (%) / Found (%)<br>C: 68.90 / 68.75<br>H: 5.53 / 5.58<br>Cl: 8.84 / 8.77<br>F: 4.74 / 4.70<br>S: 8.00 / 8.03 |
| 5 | CH₃O–⟨phenyl⟩– | CH₃– | CH₃– | –O– | 4-F | 4'-F | A | 60 | $n_D^{20}$ 1.5573<br>$C_{24}H_{24}F_2O_3$<br>Calculated (%) / Found (%)<br>C: 72.34 / 72.43<br>H: 6.07 / 6.07<br>F: 9.54 / 9.61 |
| 6 | Cl–⟨phenyl⟩– | C₂H₅– | H | –O– | 4-F | H | C | 81 | $n_D^{20}$ 1.5603<br>$C_{23}H_{22}ClFO_2$<br>Calculated (%) / Found (%)<br>C: 71.77 / 71.85<br>H: 5.76 / 5.82<br>Cl: 9.21 / 9.15<br>F: 4.94 / 4.99 |

TABLE 1-continued

| Compound No. | Substituents in General Formula [I] Ar | R¹ | R² | Y | R³ | R⁴ | Etherification Process | Yield (%) | Physical Property Values |
|---|---|---|---|---|---|---|---|---|---|
| 7 | 4-Cl-C₆H₄- | CH₃- | CH₃- | -O- | 6-Cl | H | F | 87 | $n_D^{19.5}$ 1.5854<br>$C_{23}H_{22}Cl_2O_2$<br>Calculated (%) / Found (%)<br>C: 68.83 / 68.72<br>H: 5.53 / 5.54<br>Cl: 17.67 / 17.74 |
| 8 | 4-Cl-C₆H₄- | (CH₃)₂CH- | H | -O- | 4-F | H | C | 83 | $n_D^{20}$ 1.5642<br>$C_{24}H_{24}ClFO_2$<br>Calculated (%) / Found (%)<br>C: 72.26 / 72.40<br>H: 6.06 / 6.10<br>Cl: 8.89 / 8.82<br>F: 4.76 / 4.79 |
| 9 | 4-Cl-C₆H₄- | CH₃- | CH₃- | -O- | 4-F | 3'-Cl | B | 70 | $n_D^{19.6}$ 1.5746<br>$C_{23}H_{21}Cl_2FO_2$<br>Calculated (%) / Found (%)<br>C: 65.88 / 66.03<br>H: 5.05 / 5.01<br>Cl: 16.91 / 16.82<br>F: 4.53 / 4.60 |
| 10 | 4-Cl-C₆H₄- | CH₃- | CH₃- | -O- | 4-F | H | C | 80 | $n_D^{20}$ 1.5710<br>$C_{23}H_{22}ClFO_2$<br>Calculated (%) / Found (%)<br>C: 71.77 / 71.95<br>H: 5.76 / 5.55<br>Cl: 9.21 / 9.31<br>F: 4.94 / 5.02 |
| 11 | 4-Cl-C₆H₄- | CH₃- | CH₃- | -O- | 4-F | 2'-F | A | 68 | $n_D^{20.5}$ 1.5608<br>$C_{23}H_{21}ClF_2O_2$<br>Calculated (%) / Found (%)<br>C: 68.57 / 68.47<br>H: 5.25 / 5.33<br>Cl: 8.80 / 8.76<br>F: 9.43 / 9.50 |
| 12 | 2-naphthyl | CH₃- | CH₃- | -O- | 4-F | H | B | 74 | $n_D^{20.1}$ 1.6015<br>$C_{27}H_{25}FO_2$<br>Calculated (%) / Found (%)<br>C: 80.97 / 80.90<br>H: 6.29 / 6.33<br>F: 4.74 / 4.61 |
| 13 | 4-Cl-C₆H₄- | CH₃- | CH₃- | -O- | 4-F | 4'-CH₃O | C | 75 | $n_D^{20}$ 1.5623<br>$C_{24}H_{24}ClFO_3$<br>Calculated (%) / Found (%)<br>C: 69.48 / 69.71<br>H: 5.83 / 5.74<br>Cl: 8.54 / 8.62<br>F: 4.58 / 4.63 |
| 14 | 3,4-Cl₂-C₆H₃- | CH₃- | CH₃- | -O- | 4-F | H | C | 83 | $n_D^{20}$ 1.5745<br>$C_{23}H_{21}Cl_2FO_2$<br>Calculated (%) / Found (%)<br>C: 65.88 / 65.95<br>H: 5.04 / 5.00<br>Cl: 16.91 / 16.83<br>F: 4.53 / 4.60 |

TABLE 1-continued

| Compound No. | Substituents in General Formula [I] Ar | $R^1$ | $R^2$ | Y | $R^3$ | $R^4$ | Etherification Process | Yield (%) | Physical Property Values |
|---|---|---|---|---|---|---|---|---|---|
| 15 | Cl—⟨phenyl⟩— | $CH_3$— | $CH_3$— | —O— | 4-F | 4'-Br | A | 65 | $n_D^{20}$ 1.5806 $C_{23}H_{21}BrClFO_2$ Calculated (%) / Found (%) C: 59.56 / 59.85 H: 4.56 / 4.64 Br: 17.23 / 17.01 Cl: 7.65 / 7.77 F: 4.10 / 4.00 |
| 16 | $CH_3O$—⟨phenyl⟩— | $CH_3$— | $CH_3$— | —O— | 4-F | H | E | 79 | $n_D^{20}$ 1.5630 $C_{24}H_{25}FO_3$ Calculated (%) / Found (%) C: 75.76 / 75.83 H: 6.63 / 6.69 F: 4.99 / 4.95 |
| 17 | ⟨phenyl-$CF_3$⟩— | $CH_3$— | $CH_3$— | —O— | 4-F | H | C | 75 | $n_D^{20}$ 1.5300 $C_{24}H_{22}F_4O_2$ Calculated (%) / Found (%) C: 68.89 / 68.77 H: 5.30 / 5.21 F: 18.16 / 18.24 |
| 18 | Br—⟨phenyl⟩— | $CH_3$— | $CH_3$— | —O— | 4-F | H | C | 82 | $n_D^{20}$ 1.5836 $C_{23}H_{22}BrFO_2$ Calculated (%) / Found (%) C: 64.34 / 64.19 H: 5.17 / 5.20 Br: 18.61 / 18.72 F: 4.43 / 4.40 |
| 19 | ⟨phenyl-$CH_3$⟩— | $CH_3$— | $CH_3$— | —O— | 4-F | H | D | 42 | $n_D^{20}$ 1.5582 $C_{24}H_{25}FO_2$ Calculated (%) / Found (%) C: 79.09 / 79.31 H: 6.91 / 7.02 F: 5.21 / 5.01 |
| 20 | Cl—⟨phenyl⟩— | $C_2H_5$— | $CH_3$— | —O— | 4-F | H | A | 68 | $n_D^{20}$ 1.5633 $C_{24}H_{24}ClFO_2$ Calculated (%) / Found (%) C: 72.26 / 72.36 H: 6.06 / 6.01 Cl: 8.89 / 8.95 F: 4.76 / 4.67 |
| 21 | $CHF_2O$—⟨phenyl⟩— | $CH_3$— | $CH_3$— | —O— | 4-F | H | C | 77 | $n_D^{20}$ 1.5405 $C_{24}H_{23}F_3O_3$ Calculated (%) / Found (%) C: 69.22 / 69.52 H: 5.57 / 5.29 F: 13.67 / 13.58 |
| 22 | Cl—⟨phenyl⟩— | $CH_3$— | $CH_3$— | —O— | 4-F | 3'-$CH_3$ | E | 75 | $n_D^{20}$ 1.5642 $C_{24}H_{24}ClFO_2$ Calculated (%) / Found (%) C: 72.26 / 72.40 H: 6.06 / 5.98 Cl: 8.89 / 8.97 F: 4.76 / 4.81 |
| 23 | $CH_3$—⟨phenyl⟩— | $CH_3$— | $CH_3$— | —O— | 6-Br | H | B | 69 | $n_D^{19.9}$ 1.5880 $C_{24}H_{25}BrO_2$ Calculated (%) / Found (%) C: 67.76 / 67.92 H: 5.92 / 5.75 Br: 18.79 / 18.93 |

TABLE 1-continued

| Compound No. | Substituents in General Formula [I] Ar | R¹ | R² | Y | R³ | R⁴ | Etherification Process | Yield (%) | Physical Property Values |
|---|---|---|---|---|---|---|---|---|---|
| 24 | 3,4-dichlorophenyl | CH₃— | CH₃— | —O— | 4-F | 4'-F | A | 66 | $n_D^{20}$ 1.5669<br>$C_{23}H_{20}Cl_2F_2O_2$<br>Calculated (%) / Found (%)<br>C: 63.17 / 63.31<br>H: 4.61 / 4.57<br>Cl: 16.23 / 16.40<br>F: 8.69 / 8.75 |
| 25 | 4-chlorophenyl | (CH₃)₂CH— | CH₃— | —O— | 4-F | H | G | 72 | $n_D^{19.9}$ 1.5656<br>$C_{25}H_{26}ClFO_2$<br>Calculated (%) / Found (%)<br>C: 72.72 / 72.56<br>H: 6.35 / 6.23<br>Cl: 8.85 / 8.65<br>F: 4.60 / 4.67 |
| 26 | 4-chlorophenyl | CH₃— | CH₃— | —O— | 6-Br | H | C | 84 | $n_D^{20}$ 1.5948<br>$C_{23}H_{22}BrClO_2$<br>Calculated (%) / Found (%)<br>C: 69.97 / 70.03<br>H: 4.98 / 4.87<br>Br: 17.93 / 17.99<br>Cl: 7.95 / 7.88 |
| 27 | 4-(CH₃S)phenyl | CH₃— | CH₃— | —O— | 4-F | H | E | 75 | $n_D^{19.8}$ 1.5786<br>$C_{24}H_{25}FO_2S$<br>Calculated (%) / Found (%)<br>C: 72.70 / 72.52<br>H: 6.36 / 6.30<br>F: 4.79 / 4.86<br>S: 8.07 / 8.14 |
| 28 | 4-methylphenyl | CH₃— | CH₃— | —O— | 4-F | H | B | 71 | $n_D^{20}$ 1.5611<br>$C_{24}H_{25}FO_2$<br>Calculated (%) / Found (%)<br>C: 79.09 / 79.23<br>H: 6.91 / 7.01<br>F: 5.21 / 5.42 |
| 29 | 4-fluorophenyl | CH₃— | CH₃— | —O— | 4-F | H | C | 79 | $n_D^{20}$ 1.5558<br>$C_{23}H_{22}F_2O_2$<br>Calculated (%) / Found (%)<br>C: 74.98 / 74.79<br>H: 6.02 / 5.95<br>F: 10.31 / 10.41 |
| 30 | 4-nitrophenyl | CH₃— | CH₃— | —O— | 4-F | H | C | 83 | $n_D^{20}$ 1.5793<br>$C_{23}H_{22}FNO_4$<br>Calculated (%) / Found (%)<br>C: 69.86 / 69.62<br>H: 5.61 / 5.69<br>F: 4.80 / 4.88<br>N: 3.54 / 3.47 |
| 31 | 4-methylphenyl | CH₃— | CH₃— | —O— | 6-Cl | H | B | 66 | $n_D^{19.7}$ 1.5790<br>$C_{24}H_{25}ClO_2$<br>Calculated (%) / Found (%)<br>C: 75.68 / 75.81<br>H: 6.62 / 6.50<br>Cl: 9.31 / 9.37 |
| 32 | 4-chlorophenyl | CH₃— | CH₃— | —O— | 6-F | H | E | 76 | $n_D^{20}$ 1.5681<br>$C_{23}H_{22}ClFO_2$<br>Calculated (%) / Found (%)<br>C: 71.78 / 71.95<br>H: 5.76 / 5.64<br>Cl: 9.21 / 9.33<br>F: 4.94 / 5.01 |

TABLE 1-continued

| Compound No. | Substituents in General Formula [I] Ar | $R^1$ | $R^2$ | Y | $R^3$ | $R^4$ | Etherification Process | Yield (%) | Physical Property Values |
|---|---|---|---|---|---|---|---|---|---|
| 33 | (methylenedioxyphenyl) | $CH_3-$ | $CH_3-$ | $-O-$ | 4-F | H | F | 84 | $n_D^{20.7}$ 1.5704<br>$C_{24}H_{23}FO_4$<br>Calculated (%) / Found (%)<br>C: 73.08 / 73.23<br>H: 5.88 / 5.79<br>F: 4.82 / 4.93 |
| 34 | 4-Cl-C₆H₄- | H | $C_2H_5-$ | $-O-$ | 4-F | 3'-Cl | C | 75 | $n_D^{19.8}$ 1.5692<br>$C_{23}H_{21}Cl_2FO_2$<br>Calculated (%) / Found (%)<br>C: 65.88 / 65.71<br>H: 5.05 / 5.00<br>Cl: 16.91 / 17.03<br>F: 4.53 / 4.61 |
| 35 | 4-Cl-C₆H₄- | $C_2H_5-$ | $C_2H_5-$ | $-O-$ | 4-F | H | A | 70 | $n_D^{20.2}$ 1.5668<br>$C_{25}H_{26}FO_3$<br>Calculated (%) / Found (%)<br>C: 72.72 / 72.97<br>H: 6.35 / 6.24<br>Cl: 8.59 / 8.73<br>F: 4.60 / 4.77 |
| 36 | 4-$C_2H_5O$-C₆H₄- | $CH_3-$ | $CH_3-$ | $-O-$ | 4-F | H | C | 78 | $n_D^{20.0}$ 1.5638<br>$C_{25}H_{27}FO_3$<br>Calculated (%) / Found (%)<br>C: 76.12 / 75.95<br>H: 6.90 / 6.98<br>F: 4.82 / 4.69 |
| 37 | 4-$CH_3$-C₆H₄- | $CH_3-$ | $CH_3-$ | $-O-$ | 5-Cl | H | E | 88 | $n_D^{19.4}$ 1.5784<br>$C_{24}H_{25}ClO_2$<br>Calculated (%) / Found (%)<br>C: 75.68 / 75.82<br>H: 6.62 / 6.54<br>Cl: 9.31 / 9.51 |
| 38 | 4-n-$C_5H_{11}O$-C₆H₄- | $CH_3-$ | $CH_3-$ | $-O-$ | 4-F | H | A | 60 | $n_D^{20.0}$ 1.5503<br>$C_{28}H_{33}FO_3$<br>Calculated (%) / Found (%)<br>C: 77.03 / 77.16<br>H: 7.62 / 7.56<br>F: 4.35 / 4.22 |
| 39 | 4-$C_2H_5OCH_2CH_2O$-C₆H₄- | $CH_3-$ | $CH_3-$ | $-O-$ | 4-F | H | B | 76 | $n_D^{19.7}$ 1.5495<br>$C_{27}H_{31}FO_4$<br>Calculated (%) / Found (%)<br>C: 73.95 / 73.76<br>H: 7.13 / 7.01<br>F: 4.33 / 4.24 |
| 40 | 4-$CH_3CO$-C₆H₄- | $CH_3-$ | $CH_3-$ | $-O-$ | 4-F | H | C | 79 | $n_D^{20.7}$ 1.5849<br>$C_{25}H_{25}FO_3$<br>Calculated (%) / Found (%)<br>C: 76.51 / 76.33<br>H: 6.42 / 6.37<br>F: 4.84 / 4.72 |
| 41 | 4-$(CH_3)_2CHO$-C₆H₄- | $CH_3-$ | $CH_3-$ | $-O-$ | 4-F | H | C | 82 | $n_D^{20.0}$ 1.5603<br>$C_{26}H_{29}FO_3$<br>Calculated (%) / Found (%)<br>C: 76.44 / 76.61<br>H: 7.16 / 7.07<br>F: 4.65 / 4.58 |

TABLE 1-continued

| Compound No. | Substituents in General Formula [I] Ar | R¹ | R² | Y | R³ | R⁴ | Etherification Process | Yield (%) | Physical Property Values |
|---|---|---|---|---|---|---|---|---|---|
| 42 | C₂H₅S—⟨phenyl⟩— | CH₃— | CH₃— | —O— | 4-F | H | F | 81 | $n_D^{20.0}$ 1.5821<br>$C_{25}H_{27}FO_2S$<br>Calculated (%) / Found (%)<br>C: 73.14 / 73.27<br>H: 6.63 / 6.74<br>F: 4.63 / 4.52<br>S: 7.81 / 7.68 |
| 43 | C₂H₅O—⟨phenyl⟩— | CH₃— | H | —O— | 4-F | H | B | 79 | $n_D^{19.9}$ 1.5642<br>$C_{24}H_{25}FO_3$<br>Calculated (%) / Found (%)<br>C: 75.77 / 75.91<br>H: 6.62 / 6.50<br>F: 4.99 / 4.87 |
| 44 | CH₃—⟨naphthyl⟩— | CH₃— | CH₃— | —O— | 4-F | H | F | 83 | $n_D^{20.0}$ 1.6004<br>$C_{28}H_{27}FO_2$<br>Calculated (%) / Found (%)<br>C: 81.13 / 81.02<br>H: 6.57 / 6.68<br>F: 4.58 / 4.46 |
| 45 | (CH₃)₂CHCH₂O—⟨phenyl⟩— | CH₃— | CH₃— | —O— | 4-F | H | E | 86 | $n_D^{19.4}$ 1.5505<br>$C_{27}H_{31}FO_3$<br>Calculated (%) / Found (%)<br>C: 76.75 / 76.53<br>H: 7.40 / 7.25<br>F: 4.50 / 4.41 |
| 46 | cyclohexyl-O—⟨phenyl⟩— | CH₃— | CH₃— | —O— | 4-F | H | A | 77 | $n_D^{20.2}$ 1.5395<br>$C_{29}H_{33}FO_3$<br>Calculated (%) / Found (%)<br>C: 77.65 / 77.83<br>H: 7.42 / 7.26<br>F: 4.24 / 4.11 |
| 47 | C₂H₅O—⟨phenyl⟩— | C₂H₅— | H | —O— | 4-F | H | C | 87 | $n_D^{20.2}$ 1.5570<br>$C_{25}H_{27}FO_3$<br>Calculated (%) / Found (%)<br>C: 76.12 / 76.27<br>H: 6.90 / 6.82<br>F: 4.82 / 4.74 |
| 48 | 3,5-Cl₂—⟨phenyl⟩— | CH₃— | CH₃— | —O— | 4-F | H | D | 49 | $n_D^{20.0}$ 1.5792<br>$C_{23}H_{21}Cl_2FO_2$<br>Calculated (%) / Found (%)<br>C: 71.32 / 71.55<br>H: 5.47 / 5.39<br>Cl: 18.31 / 18.52<br>F: 4.91 / 4.83 |
| 49 | n-C₄H₉O—⟨phenyl⟩— | CH₃— | CH₃— | —O— | 4-F | H | C | 81 | $n_D^{19.5}$ 1.5530<br>$C_{27}H_{31}FO_3$<br>Calculated (%) / Found (%)<br>C: 76.75 / 76.89<br>H: 7.40 / 7.53<br>F: 4.50 / 4.42 |
| 50 | 3-F,4-Cl—⟨phenyl⟩— | CH₃— | CH₃— | —O— | 4-F | H | C | 87 | $n_D^{20.4}$ 1.5679<br>$C_{23}H_{21}ClF_2O_2$<br>Calculated (%) / Found (%)<br>C: 68.32 / 68.15<br>H: 5.25 / 5.14<br>Cl: 8.80 / 8.99<br>F: 9.43 / 9.31 |

TABLE 1-continued

| Compound No. | Substituents in General Formula [I] Ar | $R^1$ | $R^2$ | Y | $R^3$ | $R^4$ | Etherification Process | Yield (%) | Physical Property Values |
|---|---|---|---|---|---|---|---|---|---|
| 51 | 2-Cl-4-(C₂H₅O)-C₆H₃- (C₂H₅O with Cl on ring) | $CH_3-$ | $CH_3-$ | $-S-$ | 4-F | H | B | 77 | $n_D^{19.8}$ 1.5882<br>$C_{25}H_{26}ClFO_2S$<br>Calculated (%) / Found (%)<br>C: 67.48 / 67.34<br>H: 5.89 / 5.96<br>Cl: 7.97 / 8.11<br>F: 4.27 / 4.18<br>S: 7.21 / 7.39 |
| 52 | C₆H₅-O-C₆H₄- | $CH_3-$ | $CH_3-$ | $-O-$ | 4-F | H | B | 75 | $n_D^{19.5}$ 1.5856<br>$C_{29}H_{27}FO_3$<br>Calculated (%) / Found (%)<br>C: 78.71 / 78.94<br>H: 6.15 / 6.02<br>F: 4.29 / 4.17 |
| 53 | 4-(C₂H₅O)-C₆H₄- | $CH_3-$ | $CH_3-$ | $-O-$ | 4-F | 4'-OC₂H₅ | E | 78 | $n_D^{20.2}$ 1.5556<br>$C_{27}H_{31}FO_4$<br>Calculated (%) / Found (%)<br>C: 73.95 / 74.07<br>H: 7.13 / 7.03<br>F: 4.33 / 4.26 |
| 54 | (CH₃)₂CH-S-C₆H₄- | $CH_3-$ | $CH_3-$ | $-O-$ | 4-F | H | B | 73 | $n_D^{19.6}$ 1.5746<br>$C_{26}H_{29}FO_2S$<br>Calculated (%) / Found (%)<br>C: 73.55 / 73.31<br>H: 6.88 / 6.80<br>F: 4.47 / 4.33<br>S: 7.55 / 7.76 |
| 55 | 4-(C₂H₅O)-C₆H₄- | $C_2H_5-$ | $CH_3-$ | $-O-$ | 4-F | H | F | 82 | $n_D^{19.9}$ 1.5598<br>$C_{26}H_{29}FO_3$<br>Calculated (%) / Found (%)<br>C: 76.44 / 76.32<br>H: 7.16 / 7.25<br>F: 4.65 / 4.60 |
| 56 | 3,4-(CH₃O)₂-C₆H₃- | $CH_3-$ | $CH_3-$ | $-O-$ | 4-F | H | C | 88 | $n_D^{20.3}$ 1.5662<br>$C_{25}H_{27}FO_4$<br>Calculated (%) / Found (%)<br>C: 73.15 / 73.33<br>H: 6.63 / 6.51<br>F: 4.63 / 4.49 |
| 57 | 3-(C₂H₅O)-C₆H₄- | $CH_3-$ | $CH_3-$ | $-O-$ | 4-F | H | B | 76 | $n_D^{19.8}$ 1.5610<br>$C_{25}H_{27}FO_3$<br>Calculated (%) / Found (%)<br>C: 76.12 / 76.01<br>H: 6.90 / 6.99<br>F: 4.82 / 4.70 |
| 58 | (CH₃)₂CH-C₆H₄- | $CH_3-$ | $CH_3-$ | $-O-$ | 4-F | H | C | 87 | $n_D^{20.1}$ 1.5579<br>$C_{26}H_{29}FO_2$<br>Calculated (%) / Found (%)<br>C: 79.56 / 79.34<br>H: 7.45 / 7.57<br>F: 4.84 / 4.69 |
| 59 | 2-Cl-4-(C₂H₅O)-C₆H₃- | $CH_3-$ | $CH_3-$ | $-O-$ | 4-F | H | F | 84 | $n_D^{19.6}$ 1.5676<br>$C_{25}H_{26}ClFO_3$<br>Calculated (%) / Found (%)<br>C: 70.00 / 70.19<br>H: 6.11 / 6.04<br>Cl: 8.27 / 8.43<br>F: 4.43 / 4.34 |

TABLE 1-continued

| Compound No. | Substituents in General Formula [I] Ar | $R^1$ | $R^2$ | Y | $R^3$ | $R^4$ | Etherification Process | Yield (%) | Physical Property Values |
|---|---|---|---|---|---|---|---|---|---|
| 60 | CH₃OCH₂S—⟨phenyl⟩— | CH₃— | CH₃— | —O— | 4-F | H | E | 79 | $n_D^{20.1}$ 1.5804<br>$C_{25}H_{27}FO_3S$<br>Calculated (%) / Found (%)<br>C: 70.40 / 70.62<br>H: 6.38 / 6.29<br>F: 4.45 / 4.37<br>S: 7.52 / 7.70 |
| 61 | ⟨biphenyl⟩— | CH₃— | CH₃— | —O— | 4-F | H | F | 83 | $n_D^{19.7}$ 1.6008<br>$C_{29}H_{27}FO_2$<br>Calculated (%) / Found (%)<br>C: 81.66 / 81.89<br>H: 6.38 / 6.27<br>F: 4.45 / 4.32 |
| 62 | C₂H₅O—⟨phenyl⟩— | (CH₃)₂CH— | H | —O— | 4-F | H | A | 73 | $n_D^{19.6}$ 1.5550<br>$C_{26}H_{29}FO_3$<br>Calculated (%) / Found (%)<br>C: 76.44 / 76.65<br>H: 7.16 / 7.02<br>F: 4.65 / 4.49 |
| 63 | (CH₃)(C₂H₅)CHO—⟨phenyl⟩— | CH₃— | CH₃— | —O— | 4-F | H | E | 79 | $n_D^{20.1}$ 1.5526<br>$C_{27}H_{31}FO_3$<br>Calculated (%) / Found (%)<br>C: 76.75 / 76.88<br>H: 7.40 / 7.34<br>F: 4.50 / 4.43 |
| 64 | C₂H₅O—⟨phenyl with CH₃O⟩— | CH₃— | CH₃— | —O— | 4-F | H | B | 83 | $n_D^{20.2}$ 1.5566<br>$C_{26}H_{29}FO_4$<br>Calculated (%) / Found (%)<br>C: 73.56 / 73.74<br>H: 6.89 / 6.77<br>F: 4.48 / 4.36 |
| 65 | n-C₃H₇O—⟨phenyl⟩— | CH₃— | CH₃— | —O— | 4-F | H | E | 85 | $n_D^{20.0}$ 1.5578<br>$C_{26}H_{29}FO_3$<br>Calculated (%) / Found (%)<br>C: 76.44 / 76.68<br>H: 7.16 / 7.30<br>F: 4.65 / 4.54 |
| 66 | I—⟨phenyl⟩— | CH₃— | CH₃— | —O— | 4-F | H | A | 70 | m.p. 59.0–61.0° C.<br>$C_{23}H_{22}FIO_2$<br>Calculated (%) / Found (%)<br>C: 58.00 / 58.15<br>H: 4.66 / 4.73<br>F: 3.99 / 3.86<br>I: 26.64 / 26.79 |
| 67 | C₂H₅O—⟨phenyl with CH₃⟩— | CH₃— | CH₃— | —O— | 4-F | H | E | 84 | $n_D^{20.1}$ 1.5574<br>$C_{26}H_{29}FO_3$<br>Calculated (%) / Found (%)<br>C: 76.44 / 76.69<br>H: 7.16 / 7.24<br>F: 4.65 / 4.51 |
| 68 | C₂H₅O—⟨phenyl⟩— | CH₃— | CH₃— | —O— | 4-F | 4′-Br | C | 85 | $n_D^{20.2}$ 1.5736<br>$C_{25}H_{26}BrFO_3$<br>Calculated (%) / Found (%)<br>C: 63.43 / 63.72<br>H: 5.54 / 5.50<br>Br: 16.88 / 16.99<br>F: 4.01 / 3.89 |

Processes for preparing starting compounds of the general formula [III] will now be described in detail with reference to the following Synthesis Examples.

SYNTHESIS EXAMPLE 10

A compound of the following formula was synthesized according to the following procedures:

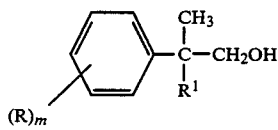

(1) A mixture of 10 g of an arylacetonitrile, 20 g of KOH, 20 g of H$_2$O and 2 g of triethylbenzyl ammonium bromide was maintained at 80° to 90° C. and methyl iodide in an amount of 1.2 moles per mole of the arylacetonitrile was added dropwise to the mixture over a period of 1 to 2 hours. Then, 10 g of KOH and 2 g of triethylbenzyl ammonium bromide were further added to the mixture. At the same temperature, a desired alkyl halide in an amount of 1.2 moles per mole of the arylacetonitrile was added dropwise to the mixture over a period of 1 to 4 hours.

The mixture was cooled to room temperature and was extracted with toluene. The intended dialkyl arylacetonitrile was obtained from the toluene extract.

(2) The dialkyl arylacetonitrile synthesized in (1) above was hydrolyzed at 130° to 150° C. with 50% H$_2$SO$_4$ or aqueous diethylene glycol/KOH to give a 2-aryl-2-alkylpropionic acid having the following formula:

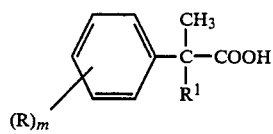

The properties of the typical compounds are shown below.

| (R')$_m$ | R$^1$ | Melting Point (°C.) |
|---|---|---|
| H | CH$_3$— | 75–76.5 |
| 3-Cl | CH$_3$— | 66.5–67.5 |
| 3,4-Cl$_2$ | CH$_3$— | 93.5–94.5 |
| 4-CH$_3$ | CH$_3$— | 80–81.5 |
| 4-Cl | C$_2$H$_5$— | 59–61.5 |
| 4-OCH$_3$ | CH$_3$— | 82.5–84 |

(3) The 2-aryl-2-alkylpropionic acid synthesized in (2) above was reduced in tetrahydrofuran with lithium aluminum hydride to obtain the intended 2-aryl-2-alkylpropyl alcohol.

SYNTHESIS EXAMPLE 11

2-(4-Chlorophenyl)-2-methylpropyl alcohol was synthesized according to the following procedures.

(1) To 169 g of chlorobenzene was added 1.5 g of ferric chloride, and hydrogen chloride gas was blown into the mixture for 10 minutes. Then, 46 g of tert-butyl chloride was added dropwise to the mixture at 30° C. over a period of 1 hour. The mixture was maintained at 30° C. for 2 hours. The reaction mixture was washed with an aqueous solution of sodium carbonate and then with water, and evaporated under reduced pressure to give 25 g of 4-tert-butylchlorobenzene (pb.: 113° C./28mmHg).

(2) To 25 g of 4-tert-butylchlorobenzene synthesized in (1) above were added 20 g of sulfuryl chloride and a catalytic amount of benzoyl peroxide, and the temperature was elevated and the mixture was maintained at 100° C. for 1 hour. Then, the mixture was distilled under reduced pressure to give 17.0 g of 2-(4-chlorophenyl)-2-methyl-1-chloropropane (bp.: 121°–123° C./10 mmHg).

(3) To 100 ml of dry tetrahydrofuran were added 2.7 g of magnesium (turnings) and a small amount of iodine as the catalyst, and 20.3 g of 2-(4-chlorophenyl)-2-methyl-1-chloropropane was added dropwise to the mixture under reflux over a period of 30 minutes. The mixture was further refluxed for 10 hours. Then, the mixture was cooled to room temperature and oxygen gas was blown into the mixture for 1 hour. Then, a saturated aqueous solution of ammonium chloride was added to the mixture and the majority of tetrahydrofuran was removed by distillation under reduced pressure. The residue was extracted with toluene, and the toluene extract was evaporated under reduced pressure to give a crude alcohol.

Recrystallization from cold hexane gave 13.3 g of 2-(4-chlorophenyl)-2-methylpropyl alcohol (mp.: 46°–48° C.).

Elementary Analysis Values as C$_{10}$H$_{13}$ClO: Calculated: C=65.04%, H=7.10%, Cl=1920% Found: C=64.18%, H=6.95%, Cl=19.16%

SYNTHESIS EXAMPLE 12

2-(3,4-Methylenedioxyphenyl)-2-methylpropyl alcohol was synthesized according to the following procedures. (1) Reaction was carried out as indicated by the following reaction formula:

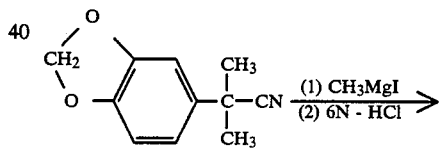

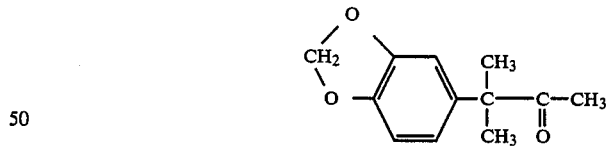

More specifically, 2.7 g of magnesium (turnings) and a small amount of iodine as the catalyst were added to 100 ml of dry ether, and 17 g of methyl iodide was gradually added dropwise to the mixture. Then, the mixture was refluxed for 30 minutes, and while the temperature was elevated, 100 ml of benzene was added to the mixture to substitute ether by benzene. Then, 18.9 g of the starting nitrile was added dropwise to the mixture under reflux.

The mixture was further refluxed for 3 hours, and then, 20 ml of 6N HCl was added dropwise to the mixture under cooling over a period of 30 minutes. Then, the temperature was elevated and the mixture was refluxed for 7 hours. Then, the mixture was cooled to room temperature, and the benzene layer was separated, washed with water, dried over Na$_2$SO$_4$, and evaporated under reduced pressure to give 19.2 g of 2-(3,4-methylenedioxyphenyl)-2-methyl-3-butanone.

$\nu_{max}^{film}$ (cm$^{-1}$): 2970, 2890, 1720, 1495, 1250, 1045, 940, 820

$\delta$CCl$_4$ (ppm): 1.38 (s, 6H), 1.85 (s, 3H), 5.91 (s, 2H), 6.67 (s, 3H).

(2) At a temperature lower than 20° C., 12.8 g of bromine was added dropwise to a mixture of 7.4 g of sodium hydroxide, 35 ml of water and 10 ml of dioxane. Then, the temperature was elevated and at 90° C., 10 g of 2-(3,4-methylenedioxyphenyl)-2-methyl-3-butanone was gradually added to the mixture, and the mixture was refluxed at 90° to 95° C. for 2 hours.

The mixture was cooled to room temperature, and a necessary amount of sodium hydrogensulfite was added to the mixture. Then, the mixture was extracted with toluene. The aqueous residual solution was made acidic with concentrated hydrochloric acid and extracted with toluene. The toluene extract was washed with water, dried over Na$_2$SO$_4$, and evaporated under reduced pressure to give 7.5 g of 2-(3,4-methylenedioxyphenyl)-2-methylpropionic acid.

$\delta$CCl$_4$ (ppm): 1.61 (s, 6H), 6.03 (s, 2H), 7.04 (s, 3H).

(3) In tetrahydrofuran, 2-(3,4-methylenedioxyphenyl)-2-methylpropionic acid was reduced with lithium aluminum hydride to give 2-(3,4-methylenedioxyphenyl)-2-methylpropyl alcohol.

$\nu_{max}^{film}$ (cm$^{-1}$): 3390, 2960, 1495, 1235, 1040, 940, 810.

$\delta$CCl$_4$ (ppm): 1.25 (s, 6H), 3.39 (s, 2H), 5.87 (s, 2H), 6.6–6.9 (m, 3H).

SYNTHESIS EXAMPLE 13

2-(4-Difluoromethoxyphenyl)-2-methylpropyl alcohol was synthesized according to the following procedures. (1) In 100 ml of acetonitrile was dissolved 18.0 g of 2,4-bis(4-hydroxyphenyl)-4-methyl-2-pentene, and 10 g of 50% NaOH was added to the solution. Then, blowing of difluorochloromethane (Freon 22) was started at 60° to 70° C. When difluorochloromethane was blown in an amount of about 60% of the amount necessary for the reaction (about 20 minutes after initiation of blowing), 10 g of 50% KOH was further added to the reaction mixture and blowing was further continued. When difluorochloromethane was blown in an amount 1.5 times the amount necessary for the reaction, blowing was stopped. The reaction mixture was cooled to room temperature and poured into 500 ml of water, and the mixture was extracted with toluene. The toluene layer was washed with water, dried over Na$_2$SO$_4$, and evaporated under reduced pressure. The obtained crude ether was purified by column chromatography on 200 g of silica gel (toluene was used as eluent) to give 19.2 g of 2,4-bis(4-difluoromethoxyphenyl)-4-methyl-2-pentene. The yield was 77%.

$n_D^{20.4}$ 1.5285.

(2) In 100 ml of acetone was dissolved 8.0 g of 2,4-bis(4-difluoromethoxyphenyl)-4-methyl-2-pentene, and 30 g of KMnO$_4$ was added to the solution at 30° C. The mixture was stirred at 30° C. for 10 hours, and 20 ml of ethyl alcohol was added dropwise to the mixture under cooling to decompose excessive KMnO$_4$. The mixture was stirred for 1 hour, and manganese dioxide formed by the reaction was removed by filtration and sufficiently washed with water and then with acetone. The filtrate was evaporated under reduced pressure, and a dilute solution of hydrochloric acid was added to the residue and the mixture was extracted with toluene. A dilute aqueous solution of NaOH was added to the toluene extract, and the mixture was sufficiently shaken and the aqueous solution layer separated, was made acidic with concentrated hydrochloric acid and extracted with toluene. The toluene extract was washed with water, dried, and evaporated under reduced pressure to give 4.2 g of intended 2-(4-difluoromethoxyphenyl)-2-methylpropionic acid (mp.: 68.5°–69.5° C.). The yield was 84%.

$\delta$CCl$_4$ (ppm): 1.58 (s, 6H), 6.42 (t, 1H, J=7 5 Hz), 7.03 (d, 2H, JAB=8.8 Hz), 7.37 (d, 2H, JAB=8.8 Hz) (AB type), 11.76 (broad s, 1H)

(3) To a mixture of 20 ml of tetrahydrofuran and 0.5 g of lithium aluminum hydride was added dropwise a solution of 2.0 g of 2-(4-difluoromethoxyphenyl)-2-methylpropionic acid in 10 ml of tetrahydrofuran at 40° C. Then, the temperature was elevated, and the mixture was refluxed for 30 minutes.

The mixture was cooled to room temperature, and ethanol was added dropwise to the mixture to decompose excessive lithium aluminum hydride. Then, water was added to the mixture to complete the decomposition. The formed precipitate was removed by filtration, and tetrahydrofuran was removed from the filtrate by distillation under reduced pressure. The residue was extracted with benzene, and the benzene extract was washed with water, dried over Na$_2$SO$_4$, and evaporated under reduced pressure to give 1.8 g of 2-(4-difluoromethoxyphenyl)-2-methylpropyl alcohol. The yield was 96%.

$\gamma_{max}^{film}$ (cm$^{-1}$): 3360, 1510, 1380, 1220, 1185, 1130, 1040, 835.

SYNTHESIS EXAMPLE 14

2-(4-Fluorophenyl)-2-methylbutyl alcohol was synthesized according to the following procedures.

(1) A 300-ml flask was charged with 16.6 g of 4-fluorotoluene, 30.0 g of NBS, 0.5 g of benzoyl peroxide and 150 ml of carbon tetrachloride, and the mixture was refluxed for 2.0 hours. The reaction mixture was cooled to room temperature, and the formed precipitate was removed by filtration and the residual CCl$_4$ solution was washed with dilute alkali and then with water, dried over Na$_2$SO$_4$, and evaporated under reduced pressure to give 28.8 g of crude 4-fluorobenzyl bromide.

A solution of 28.8 g of the so obtained crude bromide in 30 ml of ethanol was added dropwise to a mixture of 8.8 g of NaCN and 9.0 g of water at 70° to 80° C. over a period of 30 minutes. The mixture was maintained at 80° C. for 5.0 hours, and the mixture was cooled to room temperature and poured into water. Then, celite and benzene were added to the mixture and the mixture was stirred, and celite was removed by filtration. The benzene layer was separated, washed with water, dried over Na$_2$SO$_4$, and evaporated under reduced pressure to give 13.2 g of crude 4-fluorobenzyl cyanide.

$\gamma_{max}^{film}$ (cm$^{-1}$): 2270, 1615, 1520, 1430, 1240, 1170, 825.

(2) A flask was charged with 12.8 g of crude 4-fluorobenzyl cyanide, 40 g of 50% NaOH and 2 g of triethylbenzyl ammonium bromide, and while the mixture was stirred, 14 g of methyl iodide was added dropwise to the mixture at 70° C. over a period of 15 minutes.

The mixture was maintained at 70° C. for 30 minutes and was then cooled to room temperature. The mixture was poured into ice water. The mixture was extracted with benzene, and the benzene extract was washed with water, dried over Na$_2$SO$_4$, and evaporated under reduced pressure to give 13.4 g of α-methyl-4-fluorobenzyl cyanide.

A flask was charged with 7.0 g of α-methyl-4-fluorobenzyl cyanide, 15 g of KOH, 10 g of H$_2$O and 2.0 g of triethylbenzyl ammonium chloride, and 10 ml of ethyl bromide was added dropwise to the mixture under stirring at 80° C. over a period of 1 hour. The mixture was maintained at the same temperature for 2 hours. The subsequent operation was carried out in the same manner as described above to give 7.9 g of crude α-ethyl-α-methyl-4-fluorobenzyl cyanide. 7.6 g of crude α-ethyl-α-methyl-4-fluorobenzyl cyanide, 20 ml of H$_2$O and 20 ml of concentrated sulfuric acid were refluxed at 134° to 137° C. for 5.5 hours. The mixture was cooled to room temperature and extracted with benzene, and the benzene solution was extracted with dilute alkali and the obtained dilute alkali extract was adjusted to pH 7.5 with concentrated hydrochloric acid, and extracted with benzene to remove impurities. Then, the aqueous solution was adjusted to pH 4.6 with concentrated hydrochloric acid and extracted with benzene. The benzene extract was washed with water, dried over Na$_2$SO$_4$, and evaporated under reduced pressure to give 3.8 g of 2-(4-fluorophenyl)-2-methylbutyric acid.

δCDCl$_3$ (ppm): 0.85 (t, 3H, J=7 Hz), 1.55 (s, 3H), 1.8–2.3 (m, 2H), 7.0–7.6 (m, 4H), 11.3 (broad s, 1H).

(3) A solution of 3.0 g of 2-(4-fluorophenyl)-2-methylbutyric acid in 10 ml of tetrahydrofuran was added dropwise to a mixture of 20 ml of tetrahydrofuran and 0.5 g of lithium aluminum hydride at 40° C. The temperature was then elevated and the mixture was refluxed for 30 minutes. The mixture was cooled to room temperature and ethanol was added dropwise to the mixture to decompose excessive lithium aluminum hydride. Then, water was added to the mixture to complete the decomposition. The formed precipitate was removed by filtration and tetrahydrofuran was removed from the filtrate by distillation under reduced pressure. The residue was extracted with benzene, and the benzene extract was washed with water, dried over Na$_2$SO$_4$, and evaporated under reduced pressure to give 2.6 g of 2-(4-fluorophenyl)-2-methylbutyl alcohol.

n$_D^{23}$ 1.5035.

γ$_{max}^{film}$ (cm$^{-1}$): 3360, 1610, 1520, 1240, 1175, 1040, 840.

SYNTHESIS EXAMPLE 15

2-(4-Methylthiophenyl)-2-methylpropyl alcohol was synthesized according to the following procedures.

(1) Synthesis of 4-methylthiobenzyl chloride:

To 200 ml of 1,2-dichloroethane was added 18.2 g of methylal, and 61.4 g of anhydrous aluminum chloride was dissolved in the solution under cooling with water. Then, 24.8 g of thioanisole was added dropwise to the mixture at room temperature and the mixture was stirred for 3 hours to effect reaction. The reaction mixture was poured into water, and concentrated hydrochloric acid was added to dissolve solids. Then, the mixture was extracted with benzene, and the extract was washed with water and with a dilute aqueous solution of sodium hydrogencarbonate and washed with water again. Then, the extract was dried over Na$_2$SO$_4$, and evaporated to give 30.7 g of an oily residue.

(2) Synthesis of (4-methylthiophenyl)-acetonitrile:

In 12 g of water was dissolved 10.5 g of sodium cyanide, and the solution was heated at 60° C. A solution of 30.7 g of the oily product obtained in (1) above in 35 ml of ethanol was added dropwise to the above solution and the mixture was refluxed for 4 hours to effect reaction. The reaction mixture was post-treated according to conventional procedures and purified by column chromatography using benzene as eluent to give 14.7 g of (4-methylthiophenyl)-acetonitrile (oily product).

γ$_{max}^{film}$ (cm$^{-1}$): 2260, 1500, 1420, 1105, 800.

δCCl$_4$ (ppm): 2.37 (s, 3H), 3.56 (s, 2H), 7.16 (s, 4H)

(3) Synthesis of 1-(4-methylthiophenyl)-1,1-dimethylacetonitrile:

In the same manner as described in Synthesis Example 10-(1), 13.9 g of the intended product was prepared from 13.1 g of (4-methylthiophenyl)acetonitrile.

δCCl$_4$ (ppm): 1.66 (s, 6H), 2.45 (s, 3H), 7.2–7.6 (m, 4H)

(4) Synthesis of 1-(4-methylthiophenyl)-1-methylpropionic acid:

To a mixture of 5.0 g of potassium hydroxide, 5 g of water and 20 ml of diethylene glycol was added 3.8 g of 1-(4-methylthiophenyl)-1,1-dimethylacetonitrile, and reaction was carried out at 130° to 140° C. for 7 hours. The reaction mixture was cooled and poured into water. The mixture was extracted with benzene and the aqueous residual solution was made acidic with concentrated hydrochloric acid, on that occasion precipitation was caused. The mixture was extracted with ether, and the extract was washed with a saturated aqueous solution of sodium chloride, dried over Na$_2$SO$_4$, and evaporated to give 1.9 g of solid 1-(4-methylthiophenyl)-1-methylpropionic acid.

δacetone-d$_6$ (ppm): 1.54 (s, 6H), 2.43 (s, 3H), 7.0–7.5 (m, 4H)

(5) Synthesis of 2-(4-methylthiophenyl)-1-methylpropyl alcohol:

According to conventional procedures, 1.9 g of 1-(4-methylthiophenyl)-1-methylpropionic acid was reduced with lithium aluminum hydride to give 1.5 g of the desired alcohol.

δCCl$_4$ (ppm): 1.26 (s, 6H), 2.39 (s, 3H), 3.38 (s, 2H), 7.0–7.4 (m, 4H)

SYNTHESIS EXAMPLE 16

2-(4-Chlorophenyl)-2-methylpropylthiol was synthesized according to the following procedures.

(1) Synthesis of 2-(4-chlorophenyl)-2-methylpropyl tosylate:

To a mixture of 10.0 g of 2-(4-chlorophenyl)-2-methylpropyl alcohol and 20 ml of pyridine was added 10.8 g of p-toluene-sulfonyl chloride, and the mixture was reacted at 50° to 55° C. for 1 hour. The reaction mixture was poured into 100 g of ice water, and the mixture was made acidic with dilute hydrochloric acid and extracted with benzene. The benzene extract was washed with a saturated aqueous solution of sodium chloride, dried over Na$_2$SO$_4$, and evaporated under reduced pressure to give 19.3 g of a white solid residue (mp.: 69°–71.5° C.).

γ$_{max}^{KBr}$ (cm$^{-1}$): 1595, 1480, 1355, 1175, 970, 825.

δCCl$_4$ (ppm): 1.31 (s, 6H), 2.44 (s, 3H), 3.89 (s, 2H), 7.13 (s, 4H), 7.18–7.60 [m, 4H (AB type)].

(2) Synthesis of bis[2-(4-chlorophenyl)-2-methylpropyl]-disulfide:

A mixture of 13.0 g of the tosylate obtained in (1) above, 20.0 g of sodium hydrosulfide (70% purity) and 100 ml of 90% ethanol was stirred and refluxed for 3 hours to effect reaction. The reaction mixture was poured into water, and the mixture was extracted with benzene and the benzene extract was washed with water and dried over $Na_2SO_4$, and evaporated under reduced pressure to give 7.9 g of an oily residue. The oily residue was purified by silica gel column chromatography using a 1:3 mixed solvent of benzene and hexane as diluent to give 5.3 g of the desired product (oily product).

$\gamma_{max}^{film}$ (cm$^{-1}$): 2950, 1500, 1410, 1395, 1380, 1120, 1105, 1020, 830, 755.

$\delta CCl_4$ (ppm): 1.31 (s, 6H), 2.81 (s, 2H), 7.18 (d, 4H).

Elementary Analysis Values as $C_{20}H_{24}Cl_2S_2$; Calculated: C=60.17%, H=6.01%, S=16.06%, Cl=17.76%
Found: C=59.06%, H=6.07%, S=16.55%, Cl=17.56%

(3) Synthesis of 2-(4-chlorophenyl)-2-methylpropylthiol:

In 25 ml of dry ether was suspended 0.095 g of lithium aluminum hydride, and a solution of 1.0 g of bis[2-(4-chlorophenyl)-2-methylpropyl]disulfide in 10 ml of ether was added dropwise to the suspension, and the mixture was refluxed for 2 hours. The reaction mixture was poured into water and 15% dilute sulfuric acid was added, and the mixture was extracted with benzene. The benzene extract was washed with a saturated aqueous solution of soldium chloride, dried over $Na_2SO_4$, and evaporated under reduced pressure to give 1.0 g of an oily residue.

$\gamma_{max}^{film}$ (cm$^{-1}$): 2965, 2570, 1495, 1405, 1390, 1370, 1105, 1020, 830.

$\delta CCl_4$ (ppm): 0.80 (t, 1H), 1.33 (s, 6H), 2.68 (d, 2H), 7.23 (s, 4H).

Insect pests to which the insecticidal and acaricidal composition of the present invention can be applied are described below.

[SCIENTIFIC NAME - COMMON NAME]

1. Hemiptera

*Nephotettix cincticeps* Uhler-Green rice leafhopper
*Sogata furcifera* Horvath-White-backed rice planthopper
*Nilaparvata lugens* Stål-Brown rice planthopper
*Laodelphax striatellus* Fallén-Small brown planthopper
*Eurydema rugosum* Motschulsky-Cabbage bug
*Eysarcoris parvus* Uhler-White spotted spined bug
*Halyomorpha mista* Uhler-Brown-marmorated stink bug
*Lagynotomus elongatus* Dallas-Rice stink bug
*Nezara viridula* Linné-Southern green stink bug
*Cletus trigonus* Thunberg-Slender rice bug
*Stephanitis nashi* Esaki et Takeya-Japanese pear lace bug
*Stephanitis pyrioides* Scott-Azalea lace bug
*Psylla pyrisuga* Förster-Pear sucker
*Psylla mali* Schmidberger-Apple sucker
*Aleurolobus taonabae* Kuwana-Grape whitefly
*Dialeurodes citri* Ashmead-Citrus whitefly
*Trialeurodes vaporariorum* Westwood-Greenhouse whitefly
*Aphis gossypii* Glover-Cotton aphid
*Brevicoryne brassicae* Linné-Cabbage aphid
*Myzus persicae* Sulzer-Green peach aphid
*Rhopalosiphum maidis* Fitch-Corn leaf aphid
*Icerya purchasi* Maskell-Cottonycushion scale
*Planococcus citri* Risso-Citrus mealybug
*Unaspis yanonensis* Kuwana-Arrowhead scale 2. Lepidoptera

*Canephora asiatica* Staudinger-Mulberry bagworm
*Spulerina astaurcta* Meyrick-Pear bark miner
*Phyllonorycter ringoneela* Matsumura-Apple leaf miner
*Plutella xylostella* Linné-Diamond back moth
*Promalactis inopisema* Butler-Cotton seedworm
*Adoxophyes orana* Fischer von Röslerstamm-Smaller tea tortrix
*Bactra furfurana* Haworth-Mat rush worm
*Leguminivora glycinivorella* Matsumura-Soybean pod borer
*Cnaphalocrocis medinalis* Guenée-Rice leaf roller
*Etiella zinckenella* Treitschke-Lima-bean pod borer
*Ostrinia furnacalis* Guenée-Oriental corn borer
*Pleuroptya derogata* Fabricius-Cotton leaf roller
*Hyphantria cunea* Drury-Fall webworm
*Abraxas miranda* Butler-Magpie moth
*Lymantria dispar* japonica Motschulsky-Gypsy moth
*Phalera flavescens* Bremer et Grey-Cherry caterpillar
*Agrotis Segetum* Denis et Schiffermüller-Cutworm
*Helicoverpa armigera* Hübner-Cotton boll worm
*Pseudaletia separata* Walker-Armyworm
*Mamestra brassicae* Linné-Cabbage armyworm
*Plusia nigrisigna* Walker-Beet semi-looper
*Spodoptera litura* Fablicius-Common cutworm
*Parnara guttata* Bremer et Grey-Rice skipper
*Pieris rapae crucivora* Boisduval-Common cabbageworm
*Chilo suppressalis* Walker-Rice stem borer 3. Coleoptera

*Melanotus fortnumi* Candéze-Sweetpotato wireworm
*Anthrenus verbasci* Linné-Varied carpet beetle
*Tenebroides mauritanicus* Linné-Cadelle
*Lyctus brunneus* Stephens-Powder post beetle
*Henosepilachna vigintiocto punctata* Fablicius-28-Spotted lady beetle
*Monochamus alternatus* Hope-Japanese pine sawyer
*Xylotrechus pyrrhoderus* Bates-Grape borer
*Aulacophora femoralis* Motschulsky-Cucurbit leaf beetle
*Oulema oryzae* Kuwayama-Rice leaf beetle
*Phyllotreta striolata* Fablicius-Striped flea beetle
*Callosobruchus chinensis* Linné-Azuki bean weevil
*Echinochemis squameus* Billberg-Rice plant weevil
*Sitophilus oryzae* Linné-Rice weevil
*Apoderus erythrogaster* Vollenhoven-Small black leafcut weevil
*Rhynchites heros* Roelofs-Peach curculio
*Anomala cuprea* Hope-Cupreous chafer
*Popillia japonica* Newman-Japanese beetle 4. Hymenoptera

*Athalia rosae japonesis* Rohwer-Cabbage sawfly
*Arge similis* Vollenhoven-Azalea argid sawfly
*Arge pagana* Panzer-Rose argid sawfly 5. Diptera

*Tipula aino* Alexander-Rice crane fly
*Culex pipiens fatigans* Wiedemann-House mosquito
*Aedes aegypti* Linné-Yellow-fever mosquito
*Asphondylia sp.*-Soybean pod gall midge
*Hylemya antiqua* Meigen-Onion maggot
*Hylemya platura* Meigen-Seed corn maggot
*Musca domestica vicina* Macquart-House fly

*Dacus cucurbitae Coquillett*-Melon fly
*Chlorops oryzae Matsumura*-Rice stem maggot
*Agromyza oryzae Munakata*-Rice leafminer 6. Siphonaptera

*Pulex irritans Linné*-Human flea
*Xenopsylla cheopis Rothschild*-Tropical rat flea
*Ctenocephalides canis Curtis*-Dog flea 7. Thysanoptera

*Scirtothrips dorsalis Hood*-Yellow tea thrips
*Thrips tabaci Lindeman*-Onion thrips
*Chloethrips oryzae Williams*-Rice thrips 8. Anoplura

*Pediculus humanus corporis De Geer*-Body louse
*Phthirus pubis Linne*-Crab louse
*Haematopinus eurysternus Nitzsh*-Short-nosed cattle louse 9. Psocoptera

*Trogium pulsatorium Linne*-Larger pale booklouse
*Liposcelis bostrychophilus Badonnel*-Flattened booklice 10. Orthoptera

*Gryllotalpa africana palisot de Beauvois*-African mole cricket
*Locusta migratoria danica Linne*-Asiatic locust
*Oxya yezoensis Shiraki*-Short-Winged rice grass hopper 11. Dictyoptera

*Blattella germanica Linne*-German cockroach
*Periplaneta fuliginosa Serville*-Smokybrown cockroach 12. Acarina

*Boophilus microplus Canestrini*-Bull tick
*Polyphagotarsonemus latus Banks*-Broad mite
*Panonychus citri McGregor*-Citrus red mite
*Tetranychus cinnabarinus Boisduval*-Carmine spider mite
*Tetranychus urticae Koch*-Two-spotted spider mite
*Rhizoglyphus echinophus Fumouze et Robin*-Bulb mite When the compound of the present invention is actually applied, it may be used singly without incorporation of other components. Ordinarily, however, in order to facilitate the application, the compound of the present invention is mixed with a carrier to prepare an appropriate formulation and this formulation is diluted according to need before the application. No particular condition is necessary for preparing a formulation of the compound of the present invention but according to methods known to those skilled in the art of manufacture of agricultural chemicals, the compound of the present invention may optionally be prepared into any of various formulations such as emulsifiable concentrates, wettable powders, dusts, granules, fine granules, oils, aerosols, heating fumigants (mosquito coil and electric incenses), smoking agents such as fogging agents, non-heating fumigants and poisonous diets. These formulations may be applied to various uses according to intended objects.

Furthermore, it is possible to obtain an enhanced insecticidal and acaricidal effect by using two or more of the compounds of the present invention in combination. Moreover, multi-purpose compositions having excellent activities can be obtained by combining the compounds of the present invention with other physiologically active substances, for example, allethrin, N-(chrysanthemoylmethyl)-3,4,5,6-tetrahydrophthalimide, 5-benzyl-3-furylmethyl chrysanthemate, 3-phenoxybenzyl chrysanthemate, 5-propargylfurfuryl chrysanthemate, other known cyclopropanecarboxylic acid esters, such as 3-phenoxybenzyl 3-(2,2-dichlorovinyl)-2,2-dimethyl-cyclopropane-1-carboxylate, 3-phenoxy-α-cyano-benzyl 3-(2,2-dichlorovinyl)-2,2-dimethyl-cyclopropane-1-carboxylate, 3-phenoxy-α-cyano-benzyl 3-(2,2-dibromovinyl)-2,2-dimethyl-cyclopropane-1-carboxylate, other synthetic pyrethroids such as 3-phenoxy-α-cyanobenzyl α-isopropyl-4-chlorophenylacetate and isomers thereof, pyrethrum extracts, organophosphorous insecticides such as 0,0-diethyl-0-(3-oxo-2-phenyl-2H-pyridazin-6-yl)-phosphorothioate (supplied under registered tradename "Ofunack" by Mitsuitoatsu Chemicals, Inc.), 0,0-dimethyl-0-(2,2-dichlorovinyl)phosphate (DDVP), 0,0-dimethyl-0-(3-methyl-4-nitrophenyl)phosphorothioate, diazinon, 0,0-dimethyl-0-4-cyanophenylphosphorothioate, 0,0-dimethyl-S-[α-(ethoxycarbonyl)benzyl]phosphorodithioate, 2-methoxy-4H-1,3,2-benzodioxaphosphorin-2-sulfide and 0-ethyl-0-4-cyanophenyl phenyl phosphorothioate, carbamate insecticides such as 1-naphthyl-N-methylcarbamate (NAC), m-tolyl-N-methylcarbamate (MTMC), 2-dimethylamino-5,6-dimethylpyrimidin-4-yl-dimethylcarbamate (Pyrimer), 3,4-dimethylphenyl N-methylcarbamate and 2-isopropoxyphenyl N-methylcarbamate, other insecticides, acaricides, fungicides, nematocides, herbicides, plant growth regulators, fertilizers, BT agents, insect hormones and other agricultural chemicals. Furthermore, synergistic effects are expected by combining the compounds of the present invention with these physiologically active substances.

Furthermore, the effects of the compounds of the present invention can be multiplied by combining the compounds of the present invention with synergists for pyrethroids, such as α-[2-(2-butoxyethoxy)ethoxy]-4,5-methylenedioxy-2-propyltoluene (piperonyl butoxide), 1,2-methylenedioxy-4-[2-(octylsulfinyl)propyl]benzene (Sulfoxide), 4-(3,4-methylenedioxyphenyl)-5-methyl-1,3-dioxane (Safroxane), N-(2-ethylhexyl)-bicylo(2,2,1)-hepta-5-ene-2,3-dicarboxyimide (MGK-264), octachlorodipropyl ether (S-421) and isobornyl thiocyanoacetate (Sarnite). Though the compounds of the present invention are highly stable against light, heat and oxidation, compositions having much stabilized activities can be obtained by mixing the compounds of the present invention with appropriate amounts of antioxidants or ultraviolet absorbents, for example, phenol derivatives such as BHT and BHA, bisphenol derivatives, arylamines such as phenyl-α-naphthylamine, phenyl-β-naphthylamine and phenetidine, acetone condensates thereof and benzophenone type compounds, as stabilizers according to need.

In the insecticidal and acaricidal composition of the present invention, the above-mentioned ether or thioether derivative is incorporated in an amount of 0.0001 to 99% by weight, preferably 0.001 to 50% by weight.

The insecticidal and acaricidal composition of the present invention will now be described in detail with reference to the following Formulation Examples that by no means limit the scope of the present invention.

Incidentally, all of "parts" given hereinafter are by weight, and the compounds of the present invention are designated by compound numbers shown in Table 1.

FORMULATION EXAMPLE 1

A mixture of 20 parts of a compound selected from the compounds Nos. 1 through 68 shown in Table 1 (hereinafter referred to as "the compound of the present invention"), 20 parts of Sorpol SM-100 (registered Trademark for the product supplied by Toho Chemical Industrial Co., Ltd.) and 60 parts of xylol was stirred to give an emulsifiable concentrate.

FORMULATION EXAMPLE 2

In 10 parts of acetone was dissolved 1 part of the compound of the present invention, and 99 parts of clay for dusts was added to the solution and the mixture was evaporated to give a dust.

FORMULATION EXAMPLE 3

To 20 parts of the compound of the present invention was added 5 parts of a surface active agent, and the mixture was sufficiently blended and 75 parts of diatomaceous earth was added thereto. The mixture was blended in a crusher to give a wettable powder.

FORMULATION EXAMPLE 4

To 0.2 part of the compound of the present invention was added 2 parts of m-tolyl-N-methylcarbamate and 0.2 part of PAP (trademark for the property modifier supplied by Nippon Chemical Industrial Co., Ltd.) was further added. The mixture was dissolved in 10 parts of acetone and 97.6 parts of clay for dusts was added to the solution. The mixture was blended in a crusher and acetone was evaporated to give a dust.

FORMULATION EXAMPLE 5

To 0.2 part of the compound of the present invention was added 2 parts of Ofunack (Trademark for the product supplied by Mitsuitoatsu Chemicals, Inc.), and 0.2 part of PAP (described above) was further added. The mixture was dissolved in 10 parts of acetone and 97.6 parts of clay for dusts was added to the solution. The mixture was blended in a crusher and evaporated to give a dust.

FORMULATION EXAMPLE 6

To 0.1 part of the compound of the present invention was added 0.5 part of piperonyl butoxide, and the mixture was dissolved in kerosene so that the total amount was 100 parts, to give an oil solution.

FORMULATION EXAMPLE 7

To a mixture of 0.5 part of the compound of the present invention and 5 parts of Ofunack (described above) was added 5 parts of Sorpol SM-200 (described above), and the mixture was dissolved in 89.5 parts of xylol to give an emulsifiable concentrate.

FORMULATION EXAMPLE 8

A solution formed by mixing 0.4 part of the compound of the present invention and 2.0 parts of piperonyl butoxide with 6 parts of xylol and 7.6 parts of deodorized kerosene was charged in an aerosol vessel, and a valve portion was attached to the vessel and 84 parts of a propellant (liquefied petroleum gas) was fed under pressure through the valve portion to give an aerosol.

FORMULATION EXAMPLE 9

In an appropriate amount of chloroform was dissolved 0.05 g of the compound of the present invention, and the solution was uniformly adsorbed on the surface of an asbestos sheet having a size of 2.5 cm×1.5 cm×0.3 mm (thickness) to form a heating insecticidal fumigant to be placed on a hot plate.

FORMULATION EXAMPLE 10

In 20 ml of methanol was dissolved 0.5 g of the compound of the present invention, and the solution was homogeneously mixed with stirring with 99.5 g of an incense carrier (3:5:1 mixture of tub powder, pyrethrummarc powder and wood flour). Methanol was evaporated and 150 ml of water was added. The mixture was sufficiently kneaded and the kneaded mixture was molded and dried to give a mosquito coil.

FORMULATION EXAMPLE 11

To a mixture of 1 part of the compound of the present invention, 3 parts of Ofunack (described above), 2 parts of Serogen 7A (Trademark for the product supplied by Dai-ichi Kogyo Seiyaku) and 2 parts of Sunekisu (supplied by Sanyo Kokusaku Pulp) was added 92 parts of clay, and an appropriate amount of water was added and the mixture was granulated and sieved to give a granule.

In order to demonstrate that the compounds of the present invention have excellent insecticidal and acaricidal activities and they have very low toxicity to warm-blooded animals and fish, the results of Tests will now be described.

SAMPLES

To a mixture of 20 parts of the compound of the present invention and 20 parts of Sorpol SM-200 (registered trademark for the product supplied by Toho Chemical Industrial Co., Ltd.) was added 60 parts of xylol, and the mixture was sufficiently blended. The obtained emulsifiable concentrate was diluted at a predetermined concentration with distilled water, and the obtained dilution was used.

In the fish toxicity test, the test compound was dissolved in acetone to form a 1% solution, and a predetermined amount of the solution was used. In the mouse toxicity test, the test compound of the present invention was dissolved or suspended in corn oil, and a predetermined amount of the solution or suspension was used.

Compounds (a) through (i) described below were tested as comparative compounds in the same manner as the compounds of the present invention.

(a) 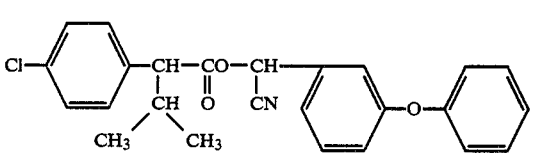

This compound is known from Japan Pesticide Information, No. 33, 13 (1977).

(b) 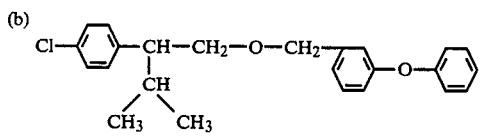

This compound is known from the specification of U.S. Pat. No. 4,073,812.
(c) Pyrethrin
(d) Ofunack (described above)
(e) MTMC (described above)
(f) Methomyl [S-methyl N-(methylcarbamoyloxy)thi-oacetoamidate]
(g) DDVP (described above)
(h) Orthorane (O,S-dimethyl N-acetylphosphoroamido-thiolate)
(i) Permethrin [3-phenoxy-α-cyanobenzyl 2,2-dimethyl-3-(2,2-dichlorovinyl)-cyclopropano-1-carboxylate]

TEST 1

(Effect of Tobacco Cutworm)

An emulsifiable concentrate of a test compound prepared according to the method described in Formulation Example 1 was diluted to a concentration of 100 or 20 ppm. Among the compounds of the present invention, the following compounds were used as the test compounds: (1), (1'), (3), (4), (6), (8), (9), (10), (11), (14), (15), (16), (17), (18), (19), (20), (21), (24), (27), (28), (29), (30), (33), (34), (35), (36), (38), (39), (40), (41), (42), (43), (47), (48), (50), (51), (52), (53), (54), (55), (56), (59), (60), (62), (63), (64), (65), (66), (67) and (68). Sweetpotato leaves were immersed in the dilution for 10 seconds, air-dried and placed in a plastic cup having a diameter of 10 cm. Then second-instar larvae of tobacco cutworm were set free in the cup. The cup was allowed to stand still in a thermostat chamber maintained at 25° C. After 48 hours, the numbers of killed and living larvae were counted and the mortality was calculated. The obtained result was expressed by an average value obtained from the mortality calculated in three test cups. Compounds of (b), (f) and (h) were tested as comparative compounds in the same manner as the compounds of the present invention.

All of the compounds of the present invention showed the mortality of 80 to 100% at the concentration of 20 ppm, and these effects were equal to or better than that of the comparative compound (f). (As to the effects of the comparative compounds, see Table 2).

TABLE 2

| Comparative Compound | Mortality (%) | |
|---|---|---|
| | 100 ppm | 20 ppm |
| (b) | 50 | 0 |
| (f) | 100 | 80 |
| (h) | 70 | 30 |

TEST 2

(Tobacco Cutworm Larva Dipping Test)

A dilution having a chemical concentration of 100 or 20 ppm was prepared in the same manner as described in Test 1.

Second-instar and fifth-instar larvae of tobacco cutworm were dipped in the dilution for 5 seconds, and the excessive dilution was removed by a filter paper. Then, the larvae were set free in a plastic cup and an artificial diet was supplied thereto. The cup was allowed to stand still in a thermostat chamber maintained at 25° C. After 24 hours, the numbers of the killed and living larvae were counted and the mortality was calculated. The test was made on three cups and the result was expressed by an average value.

The obtained results are shown in Table 3.

TABLE 3

| | Mortality (%) | | | |
|---|---|---|---|---|
| | Second-Instar Larvae | | Fifth-Instar Larvae | |
| Test Compound | 100 ppm | 20 ppm | 100 ppm | 20 ppm |
| Compound 1 | 90 | 80 | 80 | 70 |
| Compound 2 | 100 | 100 | 100 | 100 |
| Compound 6 | 100 | 90 | 100 | 85 |
| Compound 10 | 100 | 100 | 100 | 100 |
| Compound 15 | 100 | 100 | 100 | 100 |
| Compound 21 | 100 | 100 | 100 | 100 |
| Compound 29 | 100 | 100 | 100 | 100 |
| Compound 36 | 100 | 100 | 100 | 100 |
| Compound 41 | 100 | 100 | 100 | 100 |
| Compound 50 | 100 | 90 | 100 | 80 |
| Compound 59 | 100 | 100 | 100 | 100 |
| Compound 66 | 100 | 90 | 100 | 75 |
| Compound 67 | 100 | 100 | 100 | 100 |
| Comparative Compound (b) | 0 | 0 | 0 | 0 |
| Comparative Compound (f) | 100 | 30 | 80 | 0 |
| Comparative Compound (g) | 50 | 20 | 30 | 10 |

TEST 3

(Effect on Resistant Green Rice Leafhopper and Sensitive Green Rice Leafhopper)

Seedlings (having 2 to 3 leaves) of paddy rice were hydroponically cultured in a pot having a diameter of 5 cm. A chemical dilution having a concentration of 100 or 20 ppm, prepared in the same manner as described in Test 1, was applied with a sprayer at a rate of 3 ml per pot. The treated seedlings were air-dried and covered with a metal net cylinder, and female adults of resistant green rice leafhopper (collected at Nakagawara) and sensitive green rice leafhopper (collected at Chigasaki) were set, respectively, free in the pot at a density of 10 adults per pot. After of 24 hours, the numbers of killed and living adults were counted and the mortality was calculated. The test was made on three pots and the average value was calculated.

The obtained results are shown in Table 4.

TABLE 4

| | Mortality (%) | | | |
|---|---|---|---|---|
| | Green Rice Leafhopper Collected at Nakagawara | | Green Rice Leafhopper Collected at Chigasaki | |
| Test Compound | 100 ppm | 20 ppm | 100 ppm | 20 ppm |
| Compound 2 | 100 | 100 | 100 | 100 |
| Compound 3 | 100 | 90 | 100 | 80 |
| Compound 5 | 100 | 100 | 100 | 100 |
| Compound 6 | 100 | 100 | 100 | 100 |
| Compound 8 | 100 | 100 | 100 | 100 |
| Compound 10 | 100 | 100 | 100 | 100 |
| Compound 11 | 100 | 100 | 100 | 100 |
| Compound 12 | 100 | 95 | 100 | 80 |
| Compound 13 | 100 | 70 | 100 | 50 |
| Compound 17 | 100 | 100 | 100 | 90 |
| Compound 20 | 100 | 100 | 100 | 100 |
| Compound 21 | 100 | 100 | 100 | 100 |
| Compound 22 | 100 | 75 | 100 | 60 |
| Compound 28 | 100 | 100 | 100 | 100 |
| Compound 29 | 100 | 100 | 100 | 100 |
| Compound 30 | 100 | 90 | 100 | 80 |
| Compound 33 | 100 | 100 | 100 | 100 |

TABLE 4-continued

| Test Compound | Mortality (%) | | | |
|---|---|---|---|---|
| | Green Rice Leafhopper Collected at Nakagawara | | Green Rice Leafhopper Collected at Chigasaki | |
| | 100 ppm | 20 ppm | 100 ppm | 20 ppm |
| Compound 35 | 100 | 100 | 100 | 90 |
| Compound 36 | 100 | 100 | 100 | 100 |
| Compound 41 | 100 | 100 | 100 | 100 |
| Compound 43 | 100 | 100 | 100 | 100 |
| Compound 44 | 100 | 100 | 100 | 100 |
| Compound 45 | 100 | 100 | 100 | 100 |
| Compound 46 | 100 | 100 | 100 | 100 |
| Compound 48 | 100 | 100 | 100 | 100 |
| Compound 49 | 100 | 100 | 100 | 100 |
| Compound 53 | 100 | 100 | 100 | 90 |
| Compound 57 | 100 | 100 | 100 | 100 |
| Compound 58 | 100 | 100 | 100 | 100 |
| Compound 59 | 100 | 100 | 100 | 100 |
| Compound 60 | 100 | 100 | 100 | 90 |
| Compound 61 | 100 | 100 | 100 | 100 |
| Compound 62 | 100 | 100 | 100 | 100 |
| Compound 63 | 100 | 100 | 100 | 100 |
| Compound 64 | 100 | 100 | 100 | 100 |
| Compound 65 | 100 | 100 | 100 | 100 |
| Compound 66 | 100 | 100 | 100 | 100 |
| Compound 67 | 100 | 100 | 100 | 100 |
| Compound 68 | 100 | 100 | 100 | 100 |
| Comparative Compound (c) | 0 | 0 | 0 | 0 |
| Comparative Compound (d) | 20 | 10 | 90 | 40 |
| Comparative Compound (e) | 0 | 0 | 80 | 20 |

Test 4

(Effect on Diamond Back Moth)

Cabbage leaves were spread in a plastic cup, and 10 third-instar larvae of diamond back moth were set free in the cup.

A chemical dilution having a concentration of 100 or 20 ppm, prepared in the same manner as described in Test 1, was applied from an applicator at a rate of 3 ml per cup.

After scattering of the chemical dilution, the cup was covered, and after 24 hours, the numbers of killed and living larvae were counted and the mortality was calculated. The test was made on three cups and the average value was calculated.

The obtained results are shown in Table 5.

TABLE 5

| Test Compound | Mortality (%) | |
|---|---|---|
| | 100 ppm | 20 ppm |
| Compound 1 | 100 | 100 |
| Compound 2 | 100 | 100 |
| Compound 3 | 100 | 100 |
| Compound 4 | 100 | 90 |
| Compound 6 | 100 | 100 |
| Compound 10 | 100 | 100 |
| Compound 11 | 100 | 100 |
| Compound 14 | 100 | 100 |
| Compound 15 | 100 | 100 |
| Compound 16 | 100 | 80 |
| Compound 18 | 100 | 100 |
| Compound 19 | 100 | 100 |
| Compound 20 | 100 | 100 |
| Compound 21 | 100 | 100 |
| Compound 24 | 100 | 90 |
| Compound 28 | 100 | 100 |
| Compound 29 | 100 | 100 |
| Compound 36 | 100 | 100 |
| Compound 38 | 100 | 100 |
| Compound 41 | 100 | 100 |
| Compound 42 | 100 | 100 |

TABLE 5-continued

| Test Compound | Mortality (%) | |
|---|---|---|
| | 100 ppm | 20 ppm |
| Compound 45 | 100 | 80 |
| Compound 47 | 100 | 100 |
| Compound 51 | 100 | 80 |
| Compound 54 | 100 | 100 |
| Compound 55 | 100 | 100 |
| Compound 57 | 100 | 100 |
| Compound 59 | 100 | 100 |
| Compound 60 | 100 | 95 |
| Compound 62 | 100 | 100 |
| Compound 65 | 100 | 100 |
| Compound 66 | 100 | 90 |
| Compound 67 | 100 | 100 |
| Compound 68 | 100 | 100 |
| Comparative Compound (b) | 30 | 10 |
| Comparative Compound (f) | 10 | 0 |
| Comparative Compound (g) | 60 | 0 |

TEST 5

(Effect on green peach Aphid)

Seedlings (having 3 to 4 leaves) of an eggplant grown on a pot were inoculated with green peach aphids and the insects were allowed to grow. The number of the insects was counted. A chemical dilution having a concentration of 100 ppm, prepared in the same manner as described in Test 1, was applied with a spray gun at a rate of 10 ml per pot. Then, the pot was placed in a glass green house. After 24 hours, the number of living insects was counted and the mortality was calculated.

The test was made on three pots, and the average value was calculated. The obtained results are shown in Table 6. In Table 6, mark "A" indicates a mortality higher than 95%, mark "B" indicates a mortality of 80 to 95%, mark "C" indicates a mortality of 50 to 80%, and mark "D" indicates a mortality lower than 50%.

TABLE 6

| Test Compound | Insecticidal Activity |
|---|---|
| Compound 1 | A |
| Compound 2 | A |
| Compound 3 | A |
| Compound 4 | A |
| Compound 6 | A |
| Compound 10 | A |
| Compound 15 | A |
| Compound 18 | A |
| Compound 21 | A |
| Compound 25 | B |
| Compound 28 | A |
| Compound 34 | B |
| Compound 36 | A |
| Compound 38 | A |
| Compound 41 | A |
| Compound 42 | A |
| Compound 43 | A |
| Compound 44 | A |
| Compound 45 | A |
| Compound 48 | B |
| Compound 49 | A |
| Compound 51 | A |
| Compound 52 | A |
| Compound 54 | A |
| Compound 60 | A |
| Compound 61 | A |
| Compound 64 | A |
| Compound 67 | A |
| Compound 68 | A |
| Comparative Compound (b) | D |
| Comparative | D |

TABLE 6-continued

| Test Compound | Insecticidal Activity |
| --- | --- |
| Compound (g) | |
| Comparative Compound (h) | B |

TEST 6

(Effect on Two-Spotted Spider mite adults)

A kidney bean leaf disc perforated with a cork borer (15 mm in diameter) was placed on water-impreganated absorbent cotton (2 cm×2 cm), and 10 adults of two-spotted spider mite were set free. A chemical dilution having a concentration of 500 ppm was applied with an applicator in an amount of 3 ml.

The leaf disc-placed absorbent cotton was placed in a thermostat chamber maintained at 25° C. After 24 hours, the number of killed adults was counted and the mortality was calculated. The test was made on three leaf discs and the average value was calculated.

The obtained results are shown in Table 7.

TABLE 7

| Test Compound | Mortality (%) |
| --- | --- |
| Compound 1 | 100 |
| Compound 3 | 90 |
| Compound 4 | 90 |
| Compound 6 | 100 |
| Compound 10 | 100 |
| Compound 11 | 100 |
| Compound 14 | 100 |
| Compound 15 | 100 |
| Compound 18 | 100 |
| Compound 20 | 100 |
| Compound 21 | 100 |
| Compound 29 | 100 |
| Compound 38 | 100 |
| Compound 39 | 100 |
| Compound 41 | 90 |
| Compound 42 | 100 |
| Compound 44 | 95 |
| Compound 46 | 100 |
| Compound 47 | 85 |
| Compound 51 | 90 |
| Compound 52 | 100 |
| Compound 54 | 100 |
| Compound 56 | 100 |
| Compound 58 | 100 |
| Compound 61 | 100 |
| Compound 63 | 100 |
| Compound 64 | 100 |
| Compound 66 | 100 |
| Compound 67 | 100 |
| Comparative Compound (b) | 20 |
| Comparative Compound (c) | 0 |
| Comparative Compound (d) | 80 |

TEST 7

(Effect on German Cockroach)

The bottom face of a high Petri dish having a diameter of 9 cm and a height of 9 cm was treated with 50 or 10 mg/m² of a test compound and the dish was air-dried. In order to prevent the adults from escaping from the dish, the inner wall of the dish was treated with butter. Then, 10 male adults of German cockroach were set free in each dish, and the dish was placed in a thermostat chamber maintained at 25° C. After 24 hours, the number of agonized and killed adults was counted. The test was made on two dishes and the average value was calculated. The obtained results are shown in Table 8.

TABLE 8

| Test Compound | Mortality (%) | |
| --- | --- | --- |
| | 50 mg/m² | 10 mg/m² |
| Compound 1 | 100 | 100 |
| Compound 2 | 100 | 100 |
| Compound 3 | 100 | 90 |
| Compound 4 | 100 | 90 |
| Compound 6 | 100 | 100 |
| Compound 10 | 100 | 100 |
| Compound 11 | 100 | 100 |
| Compound 15 | 100 | 100 |
| Compound 16 | 100 | 90 |
| Compound 18 | 100 | 100 |
| Compound 19 | 100 | 90 |
| Compound 20 | 100 | 100 |
| Compound 21 | 100 | 100 |
| Compound 28 | 100 | 100 |
| Compound 29 | 100 | 100 |
| Compound 36 | 100 | 100 |
| Compound 38 | 100 | 100 |
| Compound 41 | 100 | 100 |
| Compound 43 | 100 | 100 |
| Compound 44 | 100 | 100 |
| Compound 45 | 100 | 90 |
| Compound 47 | 100 | 100 |
| Compound 49 | 100 | 100 |
| Compound 50 | 100 | 100 |
| Compound 51 | 100 | 100 |
| Compound 52 | 100 | 100 |
| Compound 53 | 100 | 100 |
| Compound 54 | 100 | 100 |
| Compound 55 | 100 | 100 |
| Compound 58 | 100 | 100 |
| Compound 59 | 100 | 100 |
| Compound 60 | 100 | 100 |
| Compound 61 | 100 | 85 |
| Compound 63 | 100 | 100 |
| Compound 64 | 100 | 100 |
| Compound 65 | 100 | 100 |
| Compound 66 | 100 | 100 |
| Compound 67 | 100 | 100 |
| Comparative Compound (d) | 100 | 50 |
| Comparative Compound (g) | 100 | 40 |

TEST 8

(Fish Toxicity)

A water tank having a width of 60 cm, a length of 30 cm and a height of 40 cm was filled with water, and 10 yearling carps having a body length of about 5 cm were set free in the tank and adapted to the environment in the tank. A test compound was applied so that the concentration in water was 10, 1, or 0.1 ppm. After 48 hours, the numbers of killed and living carps were counted and the influences on the fishes were examined. The obtained results are shown in Table 9.

TABLE 9

| Test Compound | Fish Toxicity, $TL_{m48}$ (ppm)* |
| --- | --- |
| Compound 1 | about 1 |
| Compound 2 | above 1 |
| Compound 3 | above 10 |
| Compound 4 | above 0.5 |
| Compound 5 | above 1 |
| Compound 6 | above 1 |
| Compound 7 | above 10 |
| Compound 9 | above 1 |
| Compound 10 | above 0.1 |
| Compound 14 | above 1 |
| Compound 15 | above 10 |
| Compound 16 | above 0.5 |
| Compound 18 | above 0.1 |
| Compound 19 | above 1 |

TABLE 9-continued

| Test Compound | Fish Toxicity, TLm$_{48}$ (ppm)* |
|---|---|
| Compound 20 | above 1 |
| Compound 24 | above 1 |
| Compound 26 | above 10 |
| Compound 28 | above 1 |
| Compound 31 | above 10 |
| Compound 38 | above 1 |
| Compound 46 | above 1 |
| Compound 48 | above 1 |
| Compound 49 | about 0.5 |
| Compound 52 | above 1 |
| Compound 60 | above 1 |
| Compound 61 | above 1 |
| Compound 68 | above 1 |
| Comparative Compound (a) | below 0.005 |
| Comparative Compound (i) | below 0.005 |

Note
*the chemical concentration at which ½ of the test fishes were killed within 48 hours

TEST 9

(Toxicity Test)

A predetermined amount of a solution or suspension of a test compound in corn oil was orally administered to male mice having a body weight of 19 to 23 g (0.2 ml per 10 g of the body weight). After 7 days, the number of killed mice was counted and the influences on the mice were examined. The obtained results are shown in Table 10.

TABLE 10

| Test Compound | Acute Toxicity at Oral Administration, LD-50* (mg/Kg) |
|---|---|
| Compound 1 | above 500 |
| Compound 2 | above 500 |
| Compound 3 | above 500 |
| Compound 4 | above 500 |
| Compound 5 | above 500 |
| Compound 6 | above 500 |
| Compound 7 | above 500 |
| Compound 8 | above 500 |
| Compound 9 | above 500 |
| Compound 10 | above 500 |
| Compound 12 | above 500 |
| Compound 13 | above 500 |
| Compound 15 | above 500 |
| Compound 18 | above 500 |
| Compound 20 | above 500 |
| Compound 26 | above 500 |
| Compound 29 | above 500 |
| Compound 31 | above 500 |
| Compound 32 | above 500 |
| Compound 35 | above 500 |
| Compound 36 | above 500 |
| Compound 37 | above 500 |
| Compound 39 | above 500 |
| Compound 40 | above 500 |
| Compound 48 | above 500 |
| Compound 51 | above 500 |
| Compound 54 | above 500 |
| Compound 56 | above 500 |
| Compound 59 | above 500 |
| Compound 61 | above 500 |
| Compound 68 | above 500 |
| Comparative Compound (a) | 260 |
| Comparative Compound (c) | 340 |
| Comparative Compound (e) | 220 |
| Comparative Compound (f) | 28 |

Note
*the amount of the chemical killing ½ of the test animals

What is claimed is:

1. 2-Arylethyl ether derivatives represented by the following general formula (I):

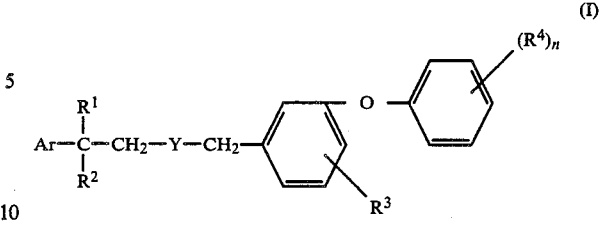

wherein:
Ar stands for an aryl group selected from the group consisting of phenyl and naphthyl groups, which are unsubstituted or substituted with the same or different substituents selected from the group consisting of
  a halogen atom;
  an unsubstituted or halogen substituted alkyl, alkoxy, alkylthio, alkenyl, alkynyl, alkenyloxy, alkynyloxy, alkoxyalkyl, alkoxyalkoxy, alkoxyalkylthio, acyl, alkoxycarbonyl, phenyl or phenoxy group;
  a cycloalkoxy, nitro, cyano, methylenedioxy, 3,4-difluoromethylenedioxy, 3,4-ethylenedioxy, 3,4-difluoroethylenedioxy or 3,4-trifluoroethylenedioxy group; and
  a polymethylene group having 3 to 5 carbon atoms;
R$_1$ stands for a straight or branched chain alkyl group of 1 to 6 carbon atoms;
R$_2$ stands for a hydrogen atom, or a methyl or ethyl group;
R$_3$ stands for a halogen atom;
R$_4$ for a hydrogen or halogen atom, or an alkyl or alkoxy group having 1 to 4 carbon atoms;
n is an integer of 1 or 2 with the proviso that when n is 2, the group R$_4$ may be the same or different; and
Y stands for an oxygen atom.

2. 2-Arylethyl ether or thioether derivatives as set forth in claim 1, wherein R$_3$ in the general formula (I) is a fluorine atom.

3. 2-Arylethyl ether derivatives as set forth in claim 1, wherein Ar in the general formula (I) is represented by the following general formula (II):

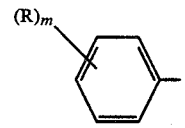

wherein
R stands for a hydrogen or halogen atom; a nitro group, a cyano group, or an unsubstituted or halogen substituted alkyl, alkoxy or alkylthio group having 1 to 6 carbon atoms; an unsubstituted or halogen substituted alkenyl, alkynyl, alkenoxy, alkynyloxy, acyl or alkoxycarbonyl group having 2 to 6 carbon atoms; a cycloalkoxy group having 3 to 6 carbon atoms; or a phenyl or phenoxy group; and
m is an integer of 1, 2, or 3, with the proviso that when m is other than 1, R may be the same or different; or the group (R)$_m$ stands for a methylenedioxy group.

4. 2-Arylethyl ether derivatives as set forth in claim 1, wherein Ar in the general formula (I) is a phenyl or naphthyl group substituted with a halogen atom, or an alkyl group having 1 to 6 carbon atoms.

5. 2-Arylethyl ether derivatives as set forth in claim 3, wherein R in the general formula (II) is a halogen atom, or an alkyl, alkoxy or haloalkoxy group having 1 to 6 carbon atoms.

6. 2-Arylethyl ether derivatives as set forth in claim 1, wherein $R^2$ in the general formula (I) is a hydrogen atom or a methyl group.

7. 2-Arylethyl ether derivatives as set forth in claim 1, wherein $R^1$ in the general formula (I) is an ethyl group or an isopropyl group, and $R^2$ in said general formula is a hydrogen atom.

8. 2-Arylethyl ether derivatives as set forth in claim 1, wherein $R^1$ in the general formula (I) is a methyl group or an ethyl group, and $R^2$ in the said general formula is a methyl group.

9. 2-Arylethyl ether derivatives as set forth in claim 1, wherein $R^3$ in the general formula (I) is a fluorine atom at the 4-position.

10. An insecticidal and acaricidal agent comprising as an active ingredient at least one member selected from the group consisting of 2-arylethyl ether derivatives represented by the following general formula (I):

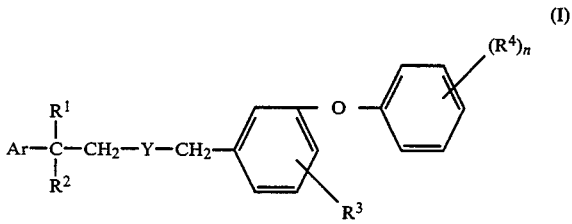

wherein:
Ar stands for an aryl group selected from the group consisting of phenyl and naphthyl groups, which are unsubstituted or substituted with the same or different substituents selected from the group consisting of -
a halogen atom;
an unsubstituted or halogen substituted alkyl, alkoxy, alkylthio, alkenyl, alkynyl, alkenyloxy, alkynyloxy, alkoxyalkyl, alkoxyalkoxy, alkoxyalkylthio, acyl, alkoxycarbonyl, phenyl or phenoxy group;
a cycloalkoxy, nitro, cyano, methylenedioxy, 3,4-difluoromethylenedioxy, 3,4-ethylenedioxy, 3,4-difluoroethylenedioxy or 3,4-trifluoroethylenedioxy group; and
a polymethylene group having 3 to 5 carbon atoms;
$R^1$ stands for a straight or branched chain alkyl group of 1 to 6 carbon atoms;
$R^2$ stands for a hydrogen atom, or a methyl or ethyl group;
$R^3$ stands for a halogen atom;
$R^4$ stands for a hydrogen or halogen atom, or an alkyl or alkoxy group having 1 to 4 carbon atoms;
n is an integer of 1 or 2 with the proviso that when n is 2, the group $R^4$ may be the same or different; and
Y stands for an oxygen atom.

11. An insecticidal and acaricidal agent in accordance with claim 10, wherein Ar in the general formula (I) is represented by the following general formula (II):

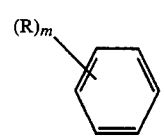

wherein R stands for a hydrogen or halogen atom; a nitro group, a cyano group, or an unsubstituted or halogen substituted alkyl, alkoxy or alkylthio group having 1 to 6 carbon atoms; an unsubstituted or halogen substituted alkenyl, alkynyl, alkenoxy, alkynyloxy, acyl or alkoxycarbonyl group having 2 to 6 carbon atoms; a cycloalkoxy group having 3 to 6 carbon atoms; or a phenyl or phenoxy group; and m is an integer of 1, 2, or 3, with the proviso that when m is other than 1, R may be the same or different; or the group $(R)_m$ stands for a methylenedioxy group.

12. An insecticidal and acaricidal agent in accordance with claim 10, wherein Ar in the general formula (I) is a phenyl or naphthyl group substituted with a halogen atom, or an alkyl group having 1 to 6 carbon atoms.

13. An insecticidal and acaricidal agent in accordance with claim 10, wherein $R^2$ in the general formula (I) is a hydrogen atom or a methyl group.

14. An insecticidal and acaricidal agent in accordance with claim 10, wherein $R^1$ in the general formula (I) is an ethyl group or an isopropyl group; and $R^2$ in said general formula is a hydrogen atom.

15. An insecticidal and acaricidal agent in accordance with claim 10, wherein $R^1$ in the general formula (I) is a methyl or an ethyl group, and $R^2$ in the said general formula is a methyl group.

16. An insecticidal and acaricidal agent in accordance with claim 10, wherein $R^3$ in the general formula (I) is a fluorine atom.

17. An insecticidal and acaricidal agent in accordance with claim 10, wherein $R^3$ in the general formula (I) is a fluorine atom at the 4-position.

18. A method for the control of insect pests and/or acarids, which comprises
applying to the locus thereof an insectidally or acaricidally effective amount of at least one compound in accordance with claim 1.

19. A method in accordance with claim 18, wherein Ar in the general formula (I) is represented by the following general formula (II):

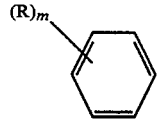

wherein R stands for a hydrogen or halogen atom; a nitro group, a cyano group, or an unsubstituted or halogen substituted alkyl, alkoxy or alkylthio group having 1 to 6 carbon atoms; an unsubstituted or halogen substituted alkenyl, alkynyl, alkenoxy, alkynyloxy, acyl or alkoxycarbonyl group having 2 to 6 carbon atoms; a cycloalkoxy group having 3 to 6 carbon atoms; or a phenyl or phenoxy group; and m is an integer of 1, 2, or 3, with the proviso that when m is other than 1, R may be the same or different; or the group $(R)_m$ stands for a methylenedioxy group.

20. A method in accordance with claim 18, wherein Ar in the general formula (I) is a phenyl or naphthyl group substituted with a halogen atom, or an alkyl group having 1 to 6 carbon atoms.

21. A method in accordance with claim 18, wherein $R^2$ in the general formula (I) is a hydrogen atom or a methyl group.

22. A method in accordance with claim 18, wherein $R^1$ in the general formula (I) is an ethyl group or an isopropyl group, and $R^2$ in said general formula is a hydrogen atom.

23. A method in accordance with claim 18, wherein $R^1$ in the general formula (I) is a methyl group or an ethyl group, and $R^2$ in said general formula is a methyl atom.

24. A method in accordance with claim 18, wherein $R^3$ in the general formula (I) is a fluorine atom.

25. A method in accordance with claim 18, wherein $R^3$ in the general formula (I) is a fluorine atom at the 4-position.

* * * * *